US006838237B2

(12) United States Patent
Fields et al.

(10) Patent No.: US 6,838,237 B2
(45) Date of Patent: Jan. 4, 2005

(54) ANTIGENICALLY REACTIVE REGIONS OF THE HEPATITIS A VIRUS POLYPROTEIN

(75) Inventors: Howard A. Fields, Marietta, GA (US); Yury E. Khudyakov, Duluth, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/171,432

(22) PCT Filed: Apr. 18, 1997

(86) PCT No.: PCT/US97/06891

§ 371 (c)(1),
(2), (4) Date: Jan. 11, 1999

(87) PCT Pub. No.: WO97/40147

PCT Pub. Date: Oct. 30, 1997

(65) Prior Publication Data

US 2003/0187184 A1 Oct. 2, 2003

Related U.S. Application Data

(60) Provisional application No. 60/015,644, filed on Apr. 19, 1996.

(51) Int. Cl.[7] .......................... C12Q 1/70; G01N 33/53; C07K 14/00; C07K 14/10

(52) U.S. Cl. ............................ 435/5; 435/7.1; 530/300; 530/324; 530/325
(58) Field of Search ........................... 424/189.1, 192.1, 424/204.1, 225.1, 226.1; 435/5, 235.1, 7.1, 7.92; 530/300, 329, 325, 326; 514/2; 536/23.72

(56) References Cited

FOREIGN PATENT DOCUMENTS

| | | |
|---|---|---|
| EP | 154587 | 9/1985 |
| WO | WO9425486 | 11/1994 |
| WO | WO9425602 | 11/1994 |

OTHER PUBLICATIONS

Bowie et al. Science, vol. 247 No. 4948, pp. 1306–1310 (1990).*
Riffkin et al., Gene, vol. 167, pp. 279–283 (1995).*
AMteu et al., Journal of General Virology, vol. 71, pp. 629–637 (1990).*

Database PIR_71 on GenCore version 4.5, Accession NoS. PQ0431, PQ0433, PQ0434, PQ0428, PQ0427, PQ0429, PQ0432, and PQ0430, 1992.*

Robertson et al. Journal of General Virology, 73:1365–1377, 1992.*
Linemeyer et al., Journal of Virology, vol. 54 No. 2 (May 1985).*
Robertson et al., Serological approaches to distinguish immune response to hepatitis A vaccine and natural infection. *Vaccine*, 10 (Suppl. 1):S106–S109 (1992).

Robertson et al., Antibody Response to Nonstructural Proteins of Hepatitis A Virus Following Infection. *J. Med. Virol.*. 40:76–82 (1993).
Jia et al., Host Antibody Response to Viral Structural and Nonstructural Proteins after Hepatitis A Virus Infection. *J. Infect. Dis.* 165:273–80 (Feb. 1992).
Khudyakov et al., Antigenic Epitopes of the Hepatitis A Virus Polyprotein. *Virology* 260:260–272 (1999).

Cohen, J. I. et al., "Complete nucleotide sequence of wild–type hepatitis A virus: comparison with different strains of hepatitis A virus and other picornaviruses," J. Virol. 61(1), 50–59 (1987). Website: GenBank Accession No. M14707, http://www.ncbi.nlm.nih.gov/entrez/viewer.fcgi?db=nucleotide&val=329582. Downloaded: Mar. 26, 2004.

Cohen, J. I. et al., "Complete nucleotide sequence of an attenuated hepatitis A virus: comparison with wild–type virus," Proc. Natl. Acad. Sci. U.S.A. 84(8), 2497–2501 (1987). Website: GenBank Accession No. M16632, http://www.ncbi.nlm.nih.gov/entrez/viewer.fcgi?db=nucleotide&val=329594. Downloaded: Apr. 26, 2004.

Lemon, S. M. et al., "Antigenic and genetic variation in cytopathic hepatitis A virus variants arising during persistent infection: evidence for genetic recombination," J. Virol. 65(4), 2056–2065 (1991). Website: GenBank Accession No. M59808, http://www.ncbi.nlm.nih.gov/entrez/viewer.fcgi?db=nucleotide&val=329585. Downloaded: Mar. 26, 2004.

Lemon, S. M. et al., "Antigenic and genetic variation in cytopathic hepatitis A virus variants arising during persistent infection: evidence for genetic recombination," J. Virol. 65(4), 2056–2065 (1991). Website: GenBank Accession No. M59809, http://www.ncbi.nlm.nih.gov/entrez/viewer.fcgi?db=nucleotide&val=329590. Downloaded: Apr. 26, 2004.

Lemon, S. M. et al., "Antigenic and genetic variation in cytopathic hepatitis A virus variants arising during persistent infection: evidence for genetic recombination," J. Virol. 65(4), 2056–2065 (1991). Website: GenBank Accession No. M59810, http://www.ncbi.nlm.nih.gov/entrez/viewer.fcgi?db=nucleotide&val=329587. Downloaded: Mar. 26, 2004.

(List continued on next page.)

*Primary Examiner*—Zachariah Lucas
(74) *Attorney, Agent, or Firm*—Needle & Rosenberg, P.C.

(57) ABSTRACT

Antigenically reactive regions of the Hepatitis A virus polyprotein are provided. These antigenically reactive regions, and polypeptides and proteins comprising these antigenically reactive regions, provide a sensitive and specific immunological hepatitis A virus detection assay. The specific use of regions derived from the nonstructural regions of the polypeptide provides the basis for determining immunity derived from prior or present infection by the Hepatitis A virus and allows one to distinguish between an immunological response derived from infection and that derived from immunization.

9 Claims, No Drawings

OTHER PUBLICATIONS

Graff, J. et al., "Nucleotide sequence of wild–type hepatitis A virus GBM in comparison with two cell culture–adapted variants," J. Virol. 68(1), 548–554 (1994). Website: GenBank Accession No. X75214, http://www.ncbi.nlm.nih.gov/entrez/viewer.fcgi?db=nucleotide&val=443844. Downloaded: Mar. 26, 2004.

Beneduce, F. et al., "Complete nucleotide sequence of a cytopathic hepatitis A virus strain isolated in Italy," Virus Res. 36(2–3), 299–309 (1995). Website: GenBank Accession No. X83302, http://www.ncbi.nlm.nih.gov/entrez/viewer.fcgi?db=nucleotide&val=603025. Downloaded: Mar. 26, 2004.

* cited by examiner

ANTIGENICALLY REACTIVE REGIONS OF THE HEPATITIS A VIRUS POLYPROTEIN

The present application is a 35 U.S.C. § 371 national phase application from, and which claims priority to, international application PCT/US97/06891, filed Apr. 18, 1997, which claims priority to U.S. provisional patent application Ser. No. 60/015,644, filed Apr. 19, 1996, which applications are hereby incorporated herein in their entirety.

BACKGROUND OF THE INVENTION

Hepatitis A virus (HAV) is a morphologically, biochemically and immunologically distinct agent which produces infectious hepatitis A in humans after an incubation period of approximately 2 to 6 weeks. Hepatitis A is a liver disease which, although not commonly fatal, can induce long periods of debilitating illness. An estimated 1.4 million cases of hepatitis A are reported annually worldwide. The disease is commonly spread by direct contact with an infected individual or by HAV-contaminated drinking water and/or food.

HAV has been characterized as a picornavirus belonging to the enterovirus group. Like other picornaviruses, HAV is 27 nm in diameter and contains a single-stranded, positive-strand infectious RNA genome coding for a single polyprotein which is subsequently processed into structural and nonstructural proteins. Four major capsid polypeptides have been described with molecular weights of 32,000 to 33,000 (VP1), 26,000 to 29,000 (VP2), 22,000 to 27,000 (VP3) and 10,000 to 14,00 (VP4). There appears to be only one serotype and significant antigenic variation has not been recognized among different HAV strains.

HAV infection is typically diagnosed by the detection of IgM or IgG antibodies to the capsid proteins. Prior art, recombinant proteins or synthetic peptides have not successfully been used as alternate sources of antigen in an enzyme immunoassay (EIA) format for the detection of anti-HAV, a serum marker of infection, because of poor antigenic reactivity due to the strictly conformational nature of HAV antigenic epitopes. For more than 15 years, the only available source of immunoreactive proteins was from HAV grown in cell culture. In fact, inactivated cell culture derived HAV is used by all commercial companies who manufacture anti-HAV tests. Unfortunately, HAV is made in very small quantities in cell culture, has a limited animal host range, and is difficult to purify from infected cell cultures and animal tissues. In addition to the inconvenience and cost associated with the production, purification and standardization of cell culture derived HAV antigen, current commercially available assays are unable to discriminate between natural infections and vaccine induced immunity as emphasized in several publications (See, e.g., Jia, et al., *J. Infect. Diseases* 165:273–280 (1992); Robertson, et al., *Vaccine* 10(Supp. 1):106–109 (1992); and Robertson, et al., *J. Med. Virol.* 40:76–82 (1993)), because these tests utilize intact HAV and therefore will detect both kinds of immune responses.

As such, there remains a need in the art for synthetic peptides which can be used as alternate sources of antigen in an enzyme immunoassay (EIA) format for the detection of anti-HAV. In addition, there remains a need in the art for methods which can be used to discriminate between vaccine-induced immunity and natural HAV immunity. Quite surprisingly, the present invention remedies such needs.

SUMMARY OF THE INVENTION

In one aspect, the present invention provides isolated, immunogenic HAV peptides corresponding to immunogenic epitopes of HAV. In one embodiment, the immununogenic peptides comprise an amino acid sequence which is substantially similar to a portion of the amino acid sequence of the VP4 protein of HAV corresponding to amino acids 1 to about 23 and a portion of the amino acid sequence of the VP2 protein of HAV virus corresponding to amino acids 24 to about 245. Such immunogenic peptides bind to an antibody specifically immunoreactive with a peptide selected from the group consisting of

| | |
|---|---|
| GLDHILSLADIEEEQMIQSV (YK-1206), | (Seq. I.D. 1); |
| DRTAVTGASYFTSVDQSSVH (YK-1208), | (Seq. I.D. 2); |
| EVGSHQVEPLRTSVDKPGSK (YK-1210), | (Seq. I.D. 3); |
| EPLRTSVDKPGSKKTQGEKF (YK-1211), | (Seq. I.D. 4); |
| DKPGSKKTQGEKFFLIHSAD (YK-1212), | (Seq. I.D. 5); |
| LYNEQFAVQGLLRYHTYARF (YK-1215), | (Seq. I.D. 6); |
| HTYARFGIEIQVQINPTPFQ (YK-1216), | (Seq. I.D. 7); |
| INPTPFQQGGLICAMVPGDQ (YK-1217), | (Seq. I.D. 8); |
| HFKDPQYPVWELTIRVWSEL (YK-1222), | (Seq. I.D. 9); |
| NIGTGTSAYTSLNVLARFRD (YK-1224). | (Seq. I.D. 10); | and conservative variations thereof.

Examples of such immunogenic HAV peptides include, but are not limited to, peptides comprising an amino acid sequence selected from the group consisting of

| | |
|---|---|
| GLDHILSLADIEEEQMIQSV (YK-1206), | (Seq. I.D. 1); |
| DRTAVTGASYFTSVDQSSVH (YK-1208), | (Seq. I.D. 2); |
| EVGSHQVEPLRTSVDKPGSK (YK-1210), | (Seq. I.D. 3); |
| EPLRTSVDKPGSKKTQGEKF (YK-1211), | (Seq. I.D. 4); |
| DKPGSKKTQGEKFFLIHSAD (YK-1212), | (Seq. I.D. 5); |
| LYNEQFAVQGLLRYHTYARF (YK-1215), | (Seq. I.D. 6); |
| HTYARFGIEIQVQINPTPFQ (YK-1216), | (Seq. I.D. 7); |
| INPTPFQQGGLICAMVPGDQ (YK-1217), | (Seq. I.D. 8); |
| HFKDPQYPVWELTIRVWSEL (YK-1222), | (Seq. I.D. 9); |
| NIGTGTSAYTSLNVLARFTD (YK-1224), | (Seq. I.D. 10); | and conservative variations thereof.

In another embodiment, the immununogenic HAV peptides comprise an amino acid sequence which is substantially similar to a portion of the VP3 protein of HAV corresponding to amino acids 246 to about 491. Such immunogenic peptides bind an antibody specifically immunoreactive with a peptide selected from the group consisting of

| | |
|---|---|
| SDPSQGGGIKITHFTTWTSI (YK-1235), | (Seq. I.D. 11); |
| GGIKITHFTTWTSIPTLAAQ (YK-1236), | (Seq. I.D. 12); |
| QFPFNASDSVGQQIKVIPVD (YK-1241), | (Seq. I.D. 13); |
| FNASDSVGQQIKVIPVDPYF (YK-1242), | (Seq. I.D. 14); |
| SDSVGQQIKVIPVDPYFFQM (YK-1243), | (Seq. I.D. 15); |
| IKVIPVDPYFFQMTNTNPDQ (YK-1244), | (Seq. I.D. 16); |

KCITALASICQMFCFWRGDL (YK-1247), (Seq. I.D. 17);

FWRGDLVFDFQVFPTKYHSG (YK-1248), (Seq. I.D. 18);

FDFQVFPTKYHSGRLLFCFV (YK-1249), (Seq. I.D. 19);

FPTKYHSGRLLFCFVPGNEL (YK-1250), (Seq. I.D. 20);

GITLKQATTAPCAVMDITGV (YK-1252), (Seq. I.D. 21);

VASHVRVNVYLSAINLECFA (YK-1261), (Seq. I.D. 22);

and conservative variations thereof. Examples of such immunogenic HAV peptides include, but are not limited to, peptides comprising an amino acid sequence selected from the group consisting of SDPSQGGGIKITHFTTWTSI (YK-1235), (Seq. I.D. 11);

GGIKITHFTTWTSIPTLAAQ (YK-1236), (Seq. I.D. 12);

QFPFNASDSVGQQIKVIPVD (YK-1241), (Seq. I.D. 13);

FNASDSVGQQIKVIPVDPYF (YK-1242), (Seq. I.D. 14);

SDSVGQQIKVIPVDPYFFQM (YK-1243), (Seq. I.D. 15);

IKVIPVDPYFFQMTNTNPDQ (YK-1244), (Seq. I.D. 16);

KCITALASICQMFCFWRGDL (YK-1247), (Seq. I.D. 17);

FWRGDLVFDFQVFPTKYHSG (YK-1248), (Seq. I.D. 18);

FDFQVFPTKYHSGRLLFCFV (YK-1249), (Seq. I.D. 19);

FPTKYHSGRLLFCFVPGNEL (YK-1250), (Seq. I.D. 20);

GITLKQATTAPCAVMDITGV (YK-1252), (Seq. I.D. 21);

VASHVRVNVYLSAINLECFA (YK-1261), (Seq. I.D. 22);

and conservative variations thereof.

In another embodiment, the immunogenic HAV peptides comprise an amino acid sequence which is substantially similar to a portion of the VP1 protein of HAV corresponding to amino acids 492 to about 791. Such immunogenic peptides bind to an antibody specifically immunoreactive with a peptide selected from the group consisting of TTVSTEQNVPDPQVGITTMK (YK-1265), (Seq. I.D. 23);

QNVPDPQVGITTMKDLKGKA (YK-1266), (Seq. I.D. 24);

NRGKMDVSGVQAPVGAITTI (YK-1268), (Seq. I.D. 25);

ITTIEDPVLAKKVPETFPEL (YK-1271), (Seq. I.D. 26);

EDPVLAKKVPETFPELKPGE (YK-1272), (Seq. I.D. 27);

AKKVPETFPELKPGESRHTS (YK-1273), (Seq. I.D. 28);

FPELKPGESRHTSDHMSIYK (YK-1274), (Seq. I.D. 29);

DHMSIYKFMGRSHFLCTFTF (YK-1276), (Seq. I.D. 30);

HFLCTFTFNSNNKEYTFPIT (YK-1279), (Seq. I.D. 31);

TPVGLAVDTPWVEKESALSI (YK-1290), (Seq. I.D. 32);

LSFSCYLSVTEQSEFYFPRA (YK-1307), (Seq. I.D. 33);

SVTEQSEFYFPRAPLNSNAM (YK-1308), (Seq. I.D. 34);

PLNSNAMLSTESMMSRIAAG (YK-1310), (Seq. I.D. 35);

MSRIAAGDLESSVDDPRSEE (YK-1312), (Seq. I.D. 36);

AGDLESSVDDPRSEEDKRFE (YK-1313), (Seq. I.D. 37);

VDDPRSEEDKRFESHIECRK (YK-1314), (Seq. I.D. 38);

and conservative variations thereof. Examples of such immunogenic HAV peptides include, but are not limited to, peptides comprising an amino acid sequence selected from the group consisting of TTVSTEQNVPDPQVGITTMK (YK-1265), (Seq. I.D. 23);

QNVPDPQVGITTMKDLKGKA (YK-1266), (Seq. I.D. 24);

NRGKMDVSGVQAPVGAITTI (YK-1268), (Seq. I.D. 25);

ITTIEDPVLAKKVPETFPEL (YK-1271), (Seq. I.D. 26);

EDPVLAKKVPETFPELKPGE (YK-1272), (Seq. I.D. 27);

AKKVPETFPELKPGESRHTS (YK-1273), (Seq. I.D. 28);

FPELKPGESRHTSDHMSIYK (YK-1274), (Seq. I.D. 29);

DHMSIYKFMGRSHFLCTFTF (YK-1276), (Seq. I.D. 30);

HFLCTFTFNSNNKEYTFPIT (YK-1279), (Seq. I.D. 31);

TPVGLAVDTPWVEKESALSI (YK-1290), (Seq. I.D. 32);

LSFSCYLSVTEQSEFYFPRA (YK-1307), (Seq. I.D. 33);

SVTEQSEFYFPRAPLNSNAM (YK-1308), (Seq. I.D. 34);

PLNSNAMLSTESMMSRIAAG (YK-1310), (Seq. I.D. 35);

MSRIAAGDLESSVDDPRSEE (YK-1312), (Seq. I.D. 36);

AGDLESSVDDPRSEEDKRFE (YK-1313), (Seq. I.D. 37);

VDDPRSEEDKRFESHIECRK (YK-1314), (Seq. I.D. 38);

and conservative variations thereof.

In a further embodiment, the immunogenic HAV peptides comprise an amino acid sequence which is substantially similar to a portion of the P2A protein of HAV corresponding to amino acids 792 to about 980. Such immunogenic peptides bind to an antibody specifically immunoreactive with a peptide selected from the group consisting of SHIECRKPYKELRLEVGKQR (YK-1315), (Seq. I.D. 39);

PYKELRLEVGKQRLKYAQEE (YK-1316), (Seq. I.D. 40);

QRLKYAQEELSNEVLPPPRK (YK-1317), (Seq. I.D. 41);

VLPPPRKMKGLFSQAKISLF (YK-1318), (Seq. I.D. 42);

FSQAKISLFYTEEHEIMKFS (YK-1319), (Seq. I.D. 43);

KVNFPHGMLDLEEIAANSKD (YK-1327), (Seq. I.D. 44);

DLEEIAANSKDFPNMSETDL (YK-1328), (Seq. I.D. 45);

KINLADRMLGLSGVQEIKEQ (YK-1331), (Seq. I.D. 46);

QRLKYAQEELSNEVLPPPRKMKGLF (YK-1665),(Seq. I.D. 47);

WLNPKKINLADRMLGLSGVQEIKEQ (YK-1757), (Seq. I.D. 48;

and conservative variations thereof. Examples of such immunogenic HAV peptides include, but are not limited to, peptides comprising an amino acid sequence selected from the group consisting of SHIECRKPYKELRLEVGKQR (YK-1315), (Seq. I.D. 39);

PYKELRLEVGKQRLKYAQEE (YK-1316), (Seq. I.D. 40);

| | |
|---|---|
| QRLKYAQEELSNEVLPPPRK (YK-1317), | (Seq. I.D. 41); |
| VLPPPRKMKGLFSQAKISLF (YK-1318), | (Seq. I.D. 42); |
| FSQAKISLFYTEEHEIMKFS (YK-1319), | (Seq. I.D. 43); |
| KVNFPHGMLDLEEIAANSKD (YK-1327), | (Seq. I.D. 44); |
| DLEEIAANSKDFPNMSETDL (YK-1328), | (Seq. I.D. 45); |
| KINLADRMLGLSGVQEIKEQ (YK-1331), | (Seq. I.D. 46); |
| QRLKYAQEELSNEVLPPPRKMKGLF (YK-1665), | (Seq. I.D. 47); |
| WLNPKKINLADRMLGLSGVQEIKEQ (YK-1757), | (Seq. I.D. 48; | and conservative variations thereof.

In another embodiment, the immunogenic HAV peptides comprise an amino acid sequence which is substantially similar to a portion of the P2B protein of HAV corresponding to amino acids 981 to about 1087. Such immunogenic peptides bind to an antibody specifically immunoreactive with a peptide selected from the group consisting of

| | |
|---|---|
| VIQQLNQDEHSHIIGLLRVM (YK-1334, | (Seq. I.D. 49); | and conservative variations thereof. Examples of such immunogenic HAV peptides include, but are not limited to, peptides comprising an amino acid sequence selected from the group consisting of

| | |
|---|---|
| VIQQLNQDEHSHIIGLLRVM (KY-1334), | (Seq. I.D. 49) | and conservative variations thereof.

In yet another embodiment, the immunogenic peptides comprise an amino acid sequence which is substantially similar to a portion of the P2C protein of HAV corresponding to amino acids 1088 to about 1422. Such immunogenic peptides bind to an antibody specifically immunoreactive with a peptide selected from the group consisting of

| | |
|---|---|
| NILKDNQQKIEKAIEEADEF (YK-1341), | (Seq. I.D. 50); |
| LGSINQAMVTRCEPVVCYLY (YK-1347), | (Seq. I.D. 51); |
| RCEPVVCYLYGKRGGGKSLT (YK-1348), | (Seq. I.D. 52); |
| TKPVASDYWDGYSGQLVCII (YK-1352), | (Seq. I.D. 53); |
| VSGCPMRLNMASLEEKGRHF (YK-1356), | (Seq. I.D. 54); |
| LNMASLEEKGRHFSSPFIIA (YK-1357), | (Seq. I.D. 55); |
| NPSPKTVYVKEAIDRRLHFK (YK-1360), | (Seq. I.D. 56); |
| VKEAIDRRLHFKVEVKPASF (YK-1361), | (Seq. I.D. 57); |
| VKPASFFKNPHNDMLNVNLA (YK-1362), | (Seq. I.D. 58); |
| KNPHNDMLNVNLAKTNDAIK (YK-1363), | (Seq. I.D. 59); |
| LAKTNDAIKDMSCVDLIMDG (YK-1364), | (Seq. I.D. 60); |
| VMTVEIRKQNMTEFMELWSQ (YK-1367), | (Seq. I.D. 61); | and conservative variations thereof. Examples of such immunogenic HAV peptides include, but are not limited to, peptides comprising an amino acid sequence selected from the group consisting of

| | |
|---|---|
| NILKDNQQKIEKAIEEADEF (YK-1341), | (Seq. I.D. 50); |
| LGSINQAMVTRCEPVVCYLY (YK-1347), | (Seq. I.D. 51); |
| RCEPVVCYLYGKRGGGKSLT (YK-1348), | (Seq. I.D. 52); |
| TKPVASDYWDGYSGQLVCII (YK-1352), | (Seq. I.D. 53); |
| VSGCPMRLNMASLEEKGRHF (YK-1356), | (Seq. I.D. 54); |
| LNMASLEEKGRHFSSPFIIA (YK-1357), | (Seq. I.D. 55); |
| NPSPKTVYVKEAIDRRLHFK (YK-1360), | (Seq. I.D. 56); |
| VKEAIDRRLHFKVEVKPASF (YK-1361), | (Seq. I.D. 57); |
| VKPASFFKNPHNDMLNVNLA (YK-1362), | (Seq. I.D. 58); |
| KNPHNDMLNVNLAKTNDAIK (YK-1363), | (Seq. I.D. 59); |
| LAKTNDAIKDMSCVDLIMDG (YK-1364), | (Seq. I.D. 60); |
| VMTVEIRKQNMTEFMELWSQ (YK-1367), | (Seq. I.D. 61); | and conservative variations thereof.

In a further embodiment, the immunogenic HAV peptides comprise an amino acid sequence which is substantially similar to a portion of the P3A protein of HAV corresponding to amino acids 1423 to about 1496. Such immunogenic peptides bind to an antibody specifically immunoreactive with a peptide selected from the group consisting of

| | |
|---|---|
| SQGISDDDNDSAVAEFFQSF (YK-1368), | (Seq. I.D. 62); |
| DSAVAEFFQSFPSGEPSNSK (YK-1369), | (Seq. I.D. 63); |
| FQSFPSGEPSNSKLSGFFQS (YK-1370), | (Seq. I.D. 64); |
| SAVAEFFQSFPSGEPSNSKLSGFFQ (YK-1832), | (Seq. I.D. 65); | and conservative variations thereof.

Examples of such immunogenic HAV peptides include, but are not limited to, peptides comprising an amino acid sequence selected from the group consisting of

| | |
|---|---|
| SQGISDDDNDSAVAEFFQSF (YK-1368), | (Seq. I.D. 62); |
| DSAVAEFFQSFPSGEPSNSK (YK-1369), | (Seq. I.D. 63); |
| FQSFPSGEPSNSKLSGFFQS (YK-1370), | (Seq. I.D. 64); |
| SAVAEFFQSFPSGEPSNSKLSGFFQ (YK-1832), | (Seq. I.D. 65); | and conservative variations thereof.

In yet a further embodiment, the immunogenic HAV peptides comprise an amino acid sequence substantially similar to a portion of the P3B protein of HAV corresponding to amino acids 1497 to about 1519. Such immunogenic peptides bind to an antibody specifically immunoreactive with a peptide selected from the group consisting of

| | |
|---|---|
| HGVTKPKQVIKLDADPVESQ (YK-1374), | (Seq. I.D. 66); | and conservative variations thereof.

Examples of such immunogenic HAV peptides include, but are not limited to, peptides comprising an amino acid sequence selected from the group consisting of

| | |
|---|---|
| HGVTKPKQVIKLDADPVESQ (YK-1374), | (Seq. I.D. 66); | and conservative variations thereof.

In yet another embodiment, the immunogenic HAV peptides comprise an amino acid sequence which is substantially similar to a portion of the P3C protein of HAV corresponding to amino acids 1520 to about 1738. Such immunogenic peptides bind to an antibody specifically immunoreactive with a peptide selected from the group consisting of GLVRKNLVQFGVGEKNGCVR (YK-1376), (Seq. I.D. 67);

DVVLMKVPTIPKFRDITQHF (YK-1382), (Seq. I.D. 68);

MEEKATYVHKKNDGTTVDLT (YK-1388), (Seq. I.D. 69);

KNDGTTVDLTVDQAWRGKGE (YK-1389), (Seq. I.D. 70);

RGKGEGLPGMCGGALVSSNQ (YK-1390), (Seq. I.D. 71);

VAKLVTQEMFQNIDKKIESQ (YK-1393), (Seq. I.D. 72);

and conservative variations thereof.

Examples of such immunogenic HAV peptides include, but are not limited to, peptides comprising an amino acid sequence selected from the group consisting of GLVRKNLVQFGVGEKNGCVR (YK-1376), (Seq. I.D. 67);

DVVLMKVPTIPKFRDITQHF (YK-1382), (Seq. I.D. 68);

MEEKATYVHKKNDGTTVDLT (YK-1388), (Seq. I.D. 69);

KNDGTTVDLTVDQAWRGKGE (YK-1389), (Seq. I.D. 70);

RGKGEGLPGMCGGALVSSNQ (YK-1390), (Seq. I.D. 71),

VAKLVTQEMFQNIDKKIESQ (YK-1393), (Seq. I.D. 72);

and conservative variations thereof.

In another aspect, the present invention provides an immunogenic composition comprising a pharmaceutically acceptable carrier and an isolated, immunogenic HAV peptide of the present invention in an amount sufficient to induce a protective immune response to HAV in a mammal. In a preferred embodiment, the immunogenic peptide is covalently attached (conjugated) to a carrier protein. Suitable carrier include, but are not limited to, serum albumin, keyhole limpet hemocyanin, diphtheria toxin, tetanus toxin and synthetic polymers (e.g., poly(D-Leu:D-Glu). As such, the present invention also provides immunogenic conjugates, such conjugates comprising: (a) a carrier protein covalently attached to (b) an isolated, immunogenic HAV peptide of the present invention.

In a further aspect, the present invention provides a method of inducing an immune response to HAV in a mammal, the method comprising administering to the mammal an immunologically effective amount of a pharmaceutical composition comprising a pharmaceutically acceptable carrier and an isolated, immunogenic HAV peptide of the present invention. In another embodiment, the present invention provides a method of detecting the presence of antibodies against HAV in mammalian serum, said method comprising: (a) contacting an isolated, immunogenic HAV peptide of the present invention with antibodies from mammalian serum; and (b) detecting the formation of complexes between the immunogenic peptide and the antibodies. In yet another embodiment, the present invention provides a method of making an antibody against HAV, the method comprising administering an immunogenic HAV peptide of the present invention to a mammal. In a further embodiment, the present invention provides a method of differentiating between vaccine-induced immunity and natural HAV immunity, the method comprising: (a) contacting an isolated, nonstructural, immunogenic HAV peptide of the present invention with antibodies from mammalian serum; and (b) detecting the formation of complexes between the immunogenic peptide and the antibodies, wherein the presence of peptide-antibody complexes indicates natural HAV immunity. Examples of suitable nonstructural immunogenic peptides suitable for use in this method of the present invention include, but are not limited to, peptides comprising an amino acid sequence selected from the group consisting of SHIECRKPYKELRLEVGKQR (YK-1315), (Seq. I.D. 39):

PYKELRLEVGKQRLKYAQEE (YK-1316), (Seq. I.D. 40);

QRLKYAQEELSNEVLPPPRK (YK-1317), (Seq. I.D. 41);

VLPPPRKMKGLFSQAKISLF (YK-1318), (Seq. I.D. 42);

FSQAKISLFYTEEHEIMKFS (YK-1319), (Seq. I.D. 43);

KVNFPHGMLDLEEIAANSKD (YK-1327), (Seq. I.D. 44);

DLEEIAANSKDFPNMSETDL (YK-1328), (Seq. I.D. 45);

KINLADRMLGLSGVQEIKEQ (YK-1331), (Seq. I.D. 46);

QRLKYAQEELSNEVLPPPRKMKGLF (YK-1665) (Seq. I.D. 47);

WLNPKKINLADRMLGLSGVQEIKEQ (YK-1757), (Seq. I.D. 48;

VIQQLNQDEHSHIIGLLRVM (YK-1334, (Seq. I.D. 49);

NILKDNQQKIEKAIEEADEF (YK-1341), (Seq. I.D. 50);

LGSINQAMVTRCEPVVCYLY (YK-1347), (Seq. I.D. 51);

RCEPVVCYLYGKRGGGKSLT (YK-1348), (Seq. I.D. 52);

TKPVASDYWDGYSGQLVCII (YK-1352), (Seq. I.D. 53);

VSGCPMRLNMASLEEKGRHF (YK-1356), (Seq. I.D. 54);

LNMASLEEKGRHFSSPFIIA (YK-1357), (Seq. I.D. 55);

NPSPKTVYYVKEAIDRRLHFK (YK-1360), (Seq. I.D. 56);

VKEAIDRRLHFKVEVKPASF (YK-1361), (Seq. I.D. 57);

VKPASFFKNPHNDMLNVNLA (YK-1362), (Seq. I.D. 58);

KNPHNDMLNVNLAKTNDAIK (YK-1363), (Seq. I.D. 59);

LAKTNDAIKDMSCVDLIMDG (YK-1364), (Seq. I.D. 60);

VMTVEIRKQNMTEFMELWSQ (YK-1367), (Seq. I.D. 61);

SQGISDDDNDSAVAEFFQSF (YK-1368), (Seq. I.D. 62);

DSAVAEFFQSFPSGEPSNSK (YK-1369), (Seq. I.D. 63);

FQSFPSGEPSNSKLSGFFQS (YK-1370), (Seq. I.D. 64);

SAVAEFFQSFPSGEPSNSKLSGFFQ (YK-1832), (Seq. I.D. 65);

HGVTKPKQVIKLDADPVESQ (YK-1374), (Seq. I.D. 66);

GLVRKNLVQFGVGEKNGCVR (YK-1376), (Seq. I.D. 67);

DVVLMKVPTIPKFRDITQHF (YK-1382), (Seq. I.D. 68);

MEEKATYVHKKNDGTTVDLT (YK-1388), (Seq. I.D. 69);

KNDGTTVDLTVDQAWRGKGE (YK-1389), (Seq. I.D. 70);

RGKGEGLPGMCGGALVSSNQ (YK-1390), (Seq. I.D. 71);

VAKLVTQEMFQNIDKKIESQ (YK-1393), (Seq. I.D. 72);

and conservative variations thereof.

In another aspect, the present invention provides isolated DNA sequences encoding a HAV immunogenic peptide having an amino acid sequence selected from the group consisting of

| Sequence | ID |
|---|---|
| GLDHILSLADIEEEQMIQSV (YK-1206), | (Seq. I.D. 1); |
| DRTAVTGASYFTSVDQSSVH (YK-1208), | (Seq. I.D. 2); |
| EVGSHQVEPLRTSVDKPGSK (YK-1210), | (Seq. I.D. 3); |
| EPLRTSVDKPGSKKTQGEKF (YK-1211), | (Seq. I.D. 4); |
| DKPGSKKTQGEKFFLIHSAD (YK-1212), | (Seq. I.D. 5); |
| LYNEQFAVQGLLRYHTYARF (YK-1215), | (Seq. I.D. 6); |
| HTYARFGIEIQVQINPTPFQ (YK-1216), | (Seq. I.D. 7); |
| INPTPFQQGGLICAMVPGDQ (YK-1217), | (Seq. I.D. 8); |
| HFKDPQYPVWELTIRVWSEL (YK-1222), | (Seq. I.D. 9); |
| NIGTGTSAYTSLNVLARFTD (YK-1224), | (Seq. I.D. 10); |
| SDPSQGGGIKITHFTTWTSI (YK-1235), | (Seq. I.D. 11); |
| GGIKITHFTTWTSIPTLAAQ (YK-1236), | (Seq. I.D. 12); |
| QFPFNASDSVGQQIKVIPVD (YK-1241), | (Seq. I.D. 13); |
| FNASDSVGQQIKVIPVDPYF (YK-1242), | (Seq. I.D. 14); |
| SDSVGQQIKVIPVDPYFFQM (YK-1243), | (Seq. I.D. 15); |
| IKVIPVDPYFFQMTNTNPDQ (YK-1244), | (Seq. I.D. 16); |
| KCITALASICQMFCFWRGDL (YK-1247), | (Seq. I.D. 17); |
| FWRGDLVFDFQVFPTKYHSG (YK-1248), | (Seq. I.D. 18); |
| FDFQVFPTKYHSGRLLFCFV (YK-1249), | (Seq. I.D. 19); |
| FPTKYHSGRLLFCFVPGNEL (YK-1250), | (Seq. I.D. 20); |
| GITLKQATTAPCAVMDITGV (YK-1252), | (Seq. I.D. 21); |
| VASHVRVNVYLSAINLECFA (YK-1261), | (Seq. I.D. 22); |
| TTVSTEQNVPDPQVGITTMK (YK-1265), | (Seq. I.D. 23); |
| QNVPDPQVGITTMKDLKGKA (YK-1266), | (Seq. I.D. 24); |
| NRGKMDVSGVQAPVGAITTI (YK-1268), | (Seq. I.D. 25); |
| ITTIEDPVLAKKVPETFPEL (YK-1271), | (Seq. I.D. 26); |
| EDPVLAKKVPETFPELKPGE (YK-1272), | (Seq. I.D. 27); |
| AKKVPETFPELKPGESRHTS (YK-1273), | (Seq. I.D. 28); |
| FPELKPGESRHTSDHMSIYK (YK-1274), | (Seq. I.D. 29); |
| DHMSIYKFMGRSHFLCTFTF (YK-1276), | (Seq. I.D. 30); |
| HFLCTFTFNSNNKEYTFPIT (YK-1279), | (Seq. I.D. 31); |
| TPVGLAVDTPWVEKESALSI (YK-1290), | (Seq. I.D. 32); |
| LSFSCYLSVTEQSEFYFPRA (YK-1307), | (Seq. I.D. 33); |
| SVTEQSEFYFPRAPLNSNAM (YK-1308), | (Seq. I.D. 34); |
| PLNSNAMLSTESMMSRIAAG (YK-1310), | (Seq. I.D. 35); |
| MSRIAAGDLESSVDDPRSEE (YK-1312), | (Seq. I.D. 36); |
| AGDLESSVDDPRSEEDKRFE (YK-1313), | (Seq. I.D. 37); |
| VDDPRSEEDKRFESHIECRK (YK-1314), | (Seq. I.D. 38); |
| SHIECRKPYKELRLEVGKQR (YK-1315), | (Seq. I.D. 39); |
| PYKELRLEVGKQRLKYAQEE (YK-1316), | (Seq. I.D. 40); |
| QRLKYAQEELSNEVLPPPRK (YK-1317), | (Seq. I.D. 41); |
| VLPPPRKMKGLFSQAKISLF (YK-1318), | (Seq. I.D. 42); |
| FSQAKISLFYTEEHEIMKFS (YK-1319), | (Seq. I.D. 43); |
| KVNFPHGMLDLEEIAANSKD (YK-1327), | (Seq. I.D. 44); |
| DLEEIAANSKDFPNMSETDL (YK-1328), | (Seq. I.D. 45); |
| KINLADRMLGLSGVQEIKEQ (YK-1331), | (Seq. I.D. 46); |
| QRLKYAQEELSNEVLPPPRKMKGLF (YK-1665), | (Seq. I.D. 47); |
| WLNPKKINLADRMLGLSGVQEIKEQ (YK-1757), | (Seq. I.D. 48; |
| VIQQLNQDEHSHIIGLLRVM (YK-1334, | (Seq. I.D. 49); |
| NILKDNQQKIEKAIEEADEF (YK-1341), | (Seq. I.D. 50); |
| LGSINQAMVTRCEPVVCYLY (YK-1347), | (Seq. I.D. 51); |
| RCEPVVCYLYGKRGGGKSLT (YK-1348), | (Seq. I.D. 52); |
| TKPVASDYWDGYSGQLVCII (YK-1352), | (Seq. I.D. 53); |
| VSGCPMRLNMASLEEKGRHF (YK-1356), | (Seq. I.D. 54); |
| LNMASLEEKGRHFSSPFIIA (YK-1357), | (Seq. I.D. 55); |
| NPSPKTVYVKEAIDRRLHFK (YK-1360), | (Seq. I.D. 56); |
| VKEAIDRRLHFKVEVKPASF (YK-1361), | (Seq. I.D. 57); |
| VKPASFFKNPHNDMLNVNLA (YK-1362), | (Seq. I.D. 58); |
| KNPHNDMLNVNLAKTNDAIK (YK-1363), | (Seq. I.D. 59); |
| LAKTNDAIKDMSCVDLIMDG (YK-1364), | (Seq. I.D. 60); |
| VMTVEIRKQNMTEFMELWSQ (YK-1367), | (Seq. I.D. 61); |
| SQGISDDDNDSAVAEFFQSF (YK-1368), | (Seq. I.D. 62); |
| DSAVAEFFQSFPSGEPSNSK (YK-1369), | (Seq. I.D. 63); |
| FQSFPSGEPSNSKLSGFFQS (YK-1370), | (Seq. I.D. 64); |
| SAVAEFFQSFPSGEPSNSKLSGFFQ (YK-1832), | (Seq. I.D. 65); |
| HGVTKPKQVIKLDADPVESQ (YK-1374), | (Seq. I.D. 66); |
| GLVRKNLVQFGVGEKNGCVR (YK-1376), | (Seq. I.D. 67); |
| DVVLMKVPTIPKFRDITQHF (YK-1382), | (Seq. I.D. 68); |
| MEEKATYVHKKNDGTTVDLT (YK-1388), | (Seq. I.D. 69): |
| KNDGTTVDLTVDQAWRGKGE (YK-1389), | (Seq. I.D. 70); |
| RGKGEGLPGMCGGALVSSNQ (YK-1390), | (Seq. I.D. 71); |
| VAKLVTQEMFQNIDKKIESQ (YK-1393), | (Seq. I.D. 72); | conservative variations thereof.

In a further aspect, the present invention provides diagnostic kits. In one embodiment, the present invention provides a kit for the diagnosis of HAV, the kit comprising a container and an isolated, immunogenic HAV peptide of the present invention. Preferably, the kit further comprises instructional materials for carrying out a diagnostic test for HAV. In another embodiment, the present invention provides a kit for differentiating between vaccine-induced immunity and natural HAV immunity, the kit comprising a container and an isolated, nonstructural immunogenic HAV peptide of the present invention. Preferably, the kit also contains instruction materials for carrying out the differentiation test.

Other features, objects and advantages of the invention and its preferred embodiments will become apparent from the detailed description which follows.

DEFINITIONS

"Peptides," "polypeptides" and "oligopeptides" are chains of amino acids (typically L-amino acids) whose a carbons are linked through peptide bonds formed by a condensation reaction between the carboxyl group of the a carbon of one amino acid and the amino group of the a carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free a-amino group on the amino acid at the amino terminal of the peptide, or to the a-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction of the carboxy terminal of the peptide. Thus, when one amino acid is said to "follow" another, that amino acid is positioned closer to the carboxy terminal of the peptide than the "preceding" amino acid.

The term "residue" is used herein to refer to an amino acid or an amino acid mimetic that is incorporated into a peptide by an amide bond or an amide bond mimetic. As such, the amino acid may be a naturally occurring amino acid or, unless otherwise limited, may encompass known analogs of natural amino acids that function in a manner similar to the naturally occurring amino acids (ie., amino acid mimetics). Moreover, an amide bond mimetic includes peptide backbone modifications well known to those skilled in the art.

The phrase "consisting essentially of" is used herein to exclude any elements that would substantially alter the essential properties of the immunogenic HAV peptides to which the phrase refers. Thus, the description of a peptide "consisting essentially of . . . " excludes any amino acid substitutions, additions, or deletions that would substantially alter the biological activity of that peptide.

"Antigen" refers to an entity or fragment thereof which can induce an immune response in a mammal. The term includes immunogens and regions responsible for antigenicity or antigenic determinants.

"Antigenic determinant" refers to a region of an HAV protein recognized by an antibody, e.g., in serum raised against wild-type HAV.

The phrases "specifically binds to a peptide" or "specifically hybridizes to" or "specifically immunoreactive with", when referring to an antibody refers to a binding reaction which is determinative of the presence of the peptide in the presence of a heterogeneous population of proteins and other biologics. Thus, under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, Harlow and Lane (1988) *Antibodies, A Laboratory Manual*, Cold Spring Harbor Publications, New York, for a description of immunoassay formats and conditions that can be used to determine specific immunoreactivity.

"Nucleic acid," as used herein, refers to a deoxyribonucleotide (DNA) or ribonucleotide (RNA) in either single- or double-stranded form, and unless otherwise limited, encompasses known analogs of natural nucleotides which can function in a manner similar to the naturally occurring nucleotides.

The phrase "nucleic acid sequence encoding" refers to a nucleic acid sequence which directs the expression of a specific protein or peptide. The nucleic acid sequences include both the DNA sequence that is transcribed into RNA and the RNA sequence that is translated into the protein. The nucleic acid sequence includes both the full length nucleic acid sequence as well as non-full length sequences derived from the full length sequence. It will be understood by those of skill that the sequence includes the degenerate codons of the native sequence or sequences which may be introduced to provide codon preference in a specific host cell.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given peptide. Such nucleic acid variations are silent, which are one species of conservatively modified variations. One of skill will recognize that each codon in a nucleic acid (except AUG, which is ordinarily the only codon for methionine) can be modified to yield a functionally identical molecule by standard techniques. Accordingly, each silent variation of a nucleic acid which encodes a peptide is implicit in any described amino acid sequence. Furthermore, one of skill will recognize that individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also Creighton (1994) *Proteins* W. H. Freeman and Company.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 432 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, PASTA, and TFASTA in the Wisconsin Genetics Software Package, Genetics Computer Group, 575 Science Dr., Madison, Wis.), or by inspection. These references are incorporated herein by reference.

The term "substantial identity" means that a polypeptide comprises a sequence that has at least 80% sequence identity, preferably 90%, more preferably 95% or more, compared to a reference sequence over a comparison window of about 10 to about 20. Another indication that polypeptide sequences are substantially identical is if one peptide is immunologically reactive with antibodies raised against the other peptide. Thus, the peptides of the invention include peptides immunologically reactive with antibodies raised against the disclose immunogenic HAV peptides.

The phrases "isolated" or "biologically pure" refer to material which is substantially or essentially free from components which normally accompany it as found in its native state. Thus, the immunogenic HAV peptides of this invention do not contain materials normally associated with their in situ environment, e.g., other proteins from a merozoite membrane. Typically, the isolated, immunogenic HAV peptides of the invention are at least about 80% pure, usually at least about 90%, and preferrably at least about 95% as measured by band intensity on a silver stained gel.

Protein purity or homogeneity may be indicated by a number of means well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or amino acid mimetic incorporated in a oligopeptide by an amide bond or amide bond mimetic. An amide bond mimetic of the invention includes peptide backbone modifications well known to those skilled in the art.

The amino acids referred to herein are described by shorthand designations as follows:

TABLE 1

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |

TABLE 1-continued

Amino Acid Nomenclature

| Name | 3-letter | 1 letter |
|---|---|---|
| Tyrosine | Tyr | Y |
| Valine | Val | V |

DETAILED DESCRIPTION OF THE INVENTION AND PREFERRED EMBODIMENTS

The present invention provides immunogenic HAV peptides corresponding to immunogenic epitopes of HAV. In addition, the present invention provides isolated DNA sequences encoding such immunogenic HAV peptides. The immunogenic HAV peptides of the present invention are capable of inducing an immune response to HAV in a mammal, i.e., they are capable of inducing the production of neutralizing antibodies against HAV in mammals. Moreover, such immunogenic HAV peptides can be used, inter alia, to detect the presence of antibodies against HAV in mammalian serum, to differentiate between vaccine-induced immunity and natural HAV immunity, or to produce an antibody against HAV. In addition, the present invention provides immunogenic compositions and vaccines made therefrom. The vaccines of the present invention comprise an immunogenic HAV peptide of the present invention, advantageously, linked to a suitable carrier molecule.

A. Peptide Synthesis

The immunogenic HAV peptides of the present invention generally comprise from about 9 to about 35 amino acid residues, more preferably, from about 15 to about 30 amino acid residues and, even more preferably, from about 20 to about 25 amino acid residues. Since the immunogenic HAV peptides of the present invention are relatively short in length, they can be prepared using any of a number of chemical peptide synthesis techniques well known to those of ordinary skill in the art including both solution methods and solid phase methods, with solid phase synthesis being presently preferred.

In particular, solid phase synthesis in which the C-terminal amino acid of the peptide sequence is attached to an insoluble support followed by sequential addition of the remaining amino acids in the sequence is the preferred method for preparing the immunogenic HAV peptides of the present invention. Techniques for solid phase synthesis are described by Barany and Merrifield, *Solid-Phase Peptide Synthesis*, in *The Peptides: Analysis, Synthesis, Biology* (Gross and Meienhofer (eds.), Academic Press, N.Y., vol. 2, pp. 3–284 (1980)); Merrifield, et al., *J. Am. Chem. Soc.* 85, 2149–2156 (1963); and Stewart, et al, *Solid Phase Peptide Synthesis* (2nd ed., Pierce Chem. Co., Rockford, Ill. (1984)), the teachings of which are hereby incorporated by reference. Many automated systems for performing solid phase peptide synthesis are commercially available.

Solid phase synthesis is started from the carboxy-terminal end (i.e., the C-terminus) of the peptide by coupling a protected amino acid via its carboxyl group to a suitable solid support. The solid support used is not a critical feature of the present invention provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for us as solid supports are well known to those of skill in the art and include, but are not limited to, the following: halomethyl resins, such as chloromethyl resin or bromomethyl resin; hydroxymethyl resins; phenol resins, such as 4-(a-[2,4-dimethoxyphenyl]-Fmoc-aminomethyl)phenoxy resin; tert-alkyloxycarbonyl-hydrazidated resins, and the like. Such resins are commercially available and their methods of preparation are known to those of ordinary skill in the art.

The acid form of the peptides of the present invention may be prepared by the solid phase peptide synthesis procedure using a benzyl ester resin as a solid support. The corresponding amides may be produced by using benzhydrylamine or methylbenzhydrylamine resin as the solid support. Those skilled in the art will recognize that when the BHA or MBHA resin is used, treatment with anhydrous hydrofluoric acid to cleave the peptide from the solid support produces a peptide having a terminal amide group.

The a-amino group of each amino acid used in the synthesis should be protected during the coupling reaction to prevent side reactions involving the reactive a-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the peptide synthesis. Protecting groups are well known to those of skill in the art. See, for example, *The Peptides: Analysis, Synthesis, Biology, Vol. 3: Protection of Functional Groups in Peptide Synthesis* (Gross and Meienhofer (eds.), Academic Press, N.Y. (1981)), the teachings of which are incorporated herein by reference.

A properly selected a-amino protecting group will render the a-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the a-amino protecting group, and must be removable after completion of the peptide synthesis under conditions that will not alter the structure of the peptide.

Illustrative examples of protecting groups for an a-amino group include, but are not limited to, the following: aromatic urethane-type groups such as, for example, fluorenylmethyloxycarbonyl (Fmoc), carbobenzoxy (Cbz), and substituted benzyloxycarbonyls including p-chlorobenzyloxycarbonyl, o-chlorobenzyloxycarbonyl, 2,4-dichlorobenzyloxycarbonyl, 2,6-dichlorobenzyloxycarbonyl, etc.; aliphatic urethane-type groups such as, for example, butyloxycarbonyl (Boc), t-amyloxycarbonyl, isopropyloxycarbonyl, 2-(p-biphenylyl)-isopopyloxycarbonyl, allyloxycarbonyl, etc.; and cycloalkyl urethane-type groups such as, for example, cyclopentyloxycarbonyl, cyclohexyloxycarbonyl, cycloheptyloxy-carbonyl, adamantyloxycarbonyl (Adoc), etc. In a presently preferred embodiment, fluorenylmethyloxycarbonyl (Fmoc) is the a-amino protecting group used.

For the side chain amino group present in lysine (Lys), any of the protecting groups described above for the protection of the a-amino group are suitable. Moreover, other suitable protecting groups include, but are not limited to, the following: butyloxycarbonyl (Boc), p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, etc. In a presently preferred embodiment, the side chain amino protecting group for Lys is butyloxycarbonyl (Boc).

For protection of the guanidino group of arginine (Arg), examples of suitable protecting groups include, but are not limited to, the following: nitro, tosyl (Tos), carbobenzoxy (Cbz), adamantyloxycarbonyl (Adoc), butyloxycarbonyl (Boc), 4-methoxy-2,3,6-trimethylbenzenesulfonyl (Mtr) and 2,2,5,7,8-pentamethylchloroman-6-sulfonyl (PMC). In a presently preferred embodiment, 4-methoxy-2,3,6-trimethylbenzenesulfonyl and 2,2,5,7,8-pentamethylchloroman-6-sulfonyl are the protecting group used for Arg.

The hydroxyl group on the side chains of serine (Ser), threonine (Thr) or tyrosine (Tyr) can be protected by a $C_1$–$C_4$ alkyl such as, for example, methyl, ethyl and t-butyl, or by a substituted benzyl such as, for example, p-methoxybenzyl, p-nitrobenzyl, p-chlorobenzyl, o-chlorobenzyl and 2,6-dichlorobenzyl. The preferred aliphatic hydroxyl protecting group for Ser, Thr and Tyr is t-butyl.

The carboxyl group of aspartic acid (Asp) may be protected by, for example, esterification using groups such as benzyl, t-butyl, cyclohexyl, cyclopentyl, and the like. For Asp, t-butyl is the presently preferred protecting group.

The basic imidazole ring in histidine (His) may be protected by, for example, t-butoxymethyl (Bom), butyloxycarbonyl (Boc) and fluorenylmethyloxycarbonyl (Fmoc). In a preferred embodiment, t-butoxymethyl (Bom) is the protecting group used.

Coupling of the amino acids may be accomplished by a variety of chemistries known to those of skill in the art. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodimide (DCC) or N,N'-diisopropylcarbodiimide (DIPCDI). Frequently, hydroxybenzotriazole (HOBt) is employed as a catalyst in these coupling reactions. Appropriate synthesis chemistries are disclosed in *The Peptides: Analysis, Structure, Biology, Vol. 1: Methods of Peptide Bond Formation* (Gross and Meienhofer (eds.), Academic Press, N.Y. (1979)); and Izurmiya, et al., *Synthesis of Peptides* (Maruzen Publishing Co., Ltd., (1975)), both of which are incorporated herein by reference.

Generally, synthesis of the peptide is commenced by first coupling the C-terminal amino acid, which is protected at the Na-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(a-[2,4-dimethoxyphenyl]-Fmoc-amino-methyl) phenoxy resin using N,N'-dicyclohexylcarbodimide (DCC) and hydroxybenzotriazole (HOBt) at about 25 EC for about two hours with stirring. Following the coupling of the Fmoc-protected amino acid to the resin support, the a-amino protecting group is removed using 20% piperidine in DMF at room temperature.

After removal of the a-amino protecting group, the remaining Fmoc-protected amino acids are coupled stepwise in the desired order. Appropriately protected amino acids are commercially available from a number of suppliers (e.g., Nova (Switzerland) or Bachem (California)). As an alternative to the stepwise addition of individual amino acids, appropriately protected peptide fragments consisting of more than one amino acid may also be coupled to the "growing" peptide. Selection of an appropriate coupling reagent, as explained above, is well known to those of skill in the art. It should be noted that since the immunogenic HAV peptides of the present invention are relative short in length, this latter approach (i.e., the segment condensation method) is not the most efficient method of peptide synthesis.

Each protected amino acid or amino acid sequence is introduced into the solid phase reactor in excess and the coupling is carried out in a medium of dimethylformamide (DMF), methylene chloride ($CH_2Cl_2$) or, mixtures thereof. If coupling is incomplete, the coupling reaction may be repeated before deprotection of the Na-amino group and addition of the next amino acid. Coupling efficiency may be monitored by a number of means well known to those of skill in the art. A preferred method of monitoring coupling efficiency is by the ninhydrin reaction. Peptide synthesis reactions may be performed automatically using a number of commercially available peptide synthesizers (e.g., Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0EC for about 20 to 90 minutes, preferably 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or, by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The peptides, i.e., the immunogenic HAV peptides of the present invention can be isolated and purified from the reaction mixture by means of peptide purification well known to those of skill in the art. For example, the immunogenic HAV peptides may be purified using known chromatographic procedures such as reverse phase HPLC, gel permeation, ion exchange, size exclusion, affinity, partition, or countercurrent distribution.

Although the immunogenic HAV peptides of the present invention are preferably prepared or produced using chemical peptide synthesis techniques such as described above, it will be understood by those of ordinary skill in the art that they can also be prepared by other means including, for example, recombinant techniques. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemlika Analytika (Fluka Chemie AG, Buchs, Switzerland), Invitrogen, San Diego, Calif., and Applied Biosystems (Foster City, Calif.), as well as many other commercial sources known to one of Skill.

The nucleic acid compositions of this invention, whether RNA, or DNA are isolated from biological sources or synthesized in vitro. The nucleic acids of the invention are present in transformed or transfected whole cells, in transformed or transfected cell lysates, or in a partially purified or substantially pure form.

In vitro amplification techniques suitable for amplifying sequences for generating nucleic acid fragments for subsequent subcloning are known. Examples of techniques sufficient to direct persons of skill through such in vitro amplification methods, including the polymerase chain reaction (PCR) the ligase chain reaction (LCR), Qb-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Small nucleic acids (less than 100 nucleotides in length) are typically synthesized chemically according to the solid phase phosphoramidite triester method described by Beaucage and Caruthers (1981), *Tetrahedron Letts.,* 22(20):1859–1862, e.g., using an automated synthesizer, as described in Needham-VanDevanter et al. (1984) *Nucleic Acids Res.,* 12:6159–6168. Nucleic acids can also be custom made and ordered from a variety of commercial sources known to persons of skill. Purification, where necessary, is typically performed by either native acrylamide gel electrophoresis or by anion-exchange HPLC as described in Pearson and Regnier (1983) *J. Chrom.* 255:137–149. The sequence of synthetic oligonucleotides can be verified using the chemical degradation method of Maxam and Gilbert (1980) in Grossman and Moldave (eds.) Academic Press, New York, *Methods in Enzymology* 65:499–560.

B. Nucleic Acid Encoding Immunogenic HAV Peptides

The immunogenic HAV peptides of the present invention are derived from proteins of known sequence which are, in turn, encoded by nucleic acids of known sequence. The entire HAV genomic sequence has been deposited with GeneBank. Access to the HAV nucleic acid can be obtained through from GeneBank by reference to the following accession numbers: X75214; X83302; M14707; M59808; M59810; M59809; and M16632.

The immunogenic HAV peptide sequences disclosed herein also provide corresponding nucleic acids which encode the given peptide. Provided with a peptide sequence of the invention, one of skill will recognize a variety of equivalent nucleic acids which encode the peptide. This is because the genetic code requires that each amino acid residue in a peptide is specified by at least one triplet of nucleotides in a nucleic acid which encodes the peptide. Due to the degeneracy of the genetic code, many amino acids are equivalently coded by more than on triplet of nucleotides. For instance, the triplets CGU, CGC, CGA, CGG, AGA, and AGG all encode the amino acid arginine. Thus, at every position where an arginine is to be encoded by a nucleic acid triplet, the nucletic acid has any of the triplets which encode arginine. One of skill is thoroughly familiar with the genetic code and its use. An introduction to the subject is found in, for example, chapter 15 of Watson, it al., *Molecular Biology of the Gene* (Fourth Edition , The Benjamin/Cummings Company, Inc., Menlo Park, Calif. (1987)), and the references cited therein, the teachings of which are incorporated herein by reference for all purposes.

Although any nucleic acid triplet or Acodon which encodes an amino acid can be used to specify the position of the amino acid in a peptide, certain codons are preferred. It is desirable to select codons for elevated expression of an encoded peptide, for example, when the peptide is purified for use as an immunogenic reagent. Codons are selected by reference to species codon bias tables, which show which codons are most typically used by the organism in which the peptide is to be expressed. The codons used frequently by an organism are translated by the more abundant t-RNAs in the cells of the organism. Because the t-RNAs are abundant, translation of the nucleic acid into a peptide by the cellular translation machinery is facilitated. Codon bias tables are available for most organisms. For an introduction to codon bias tables, see, e.g., Watson, et al., supra.

C. Making Conservative Substitutions

In addition, it will be readily apparent to those of ordinary skill in the art that the immunogenic HAV peptides of the present invention and the nucleic acid encoding such immunogenic peptides can be subject to various changes, such as insertions, deletions, and substitutions, either conservative or non-conservative, where such changes might provide for certain advantages in their use, i.e., to increase biological activity.

One of skill will appreciate that many conservative variations of nucleic acid constructs yield a functionally identical construct. For example, due to the degeneracy of the genetic code, Asilent substitutions (i.e., substitutions of a nucleic acid sequence which do not result in an alteration in an encoded peptide) are an implied feature of every nucleic acid sequence which encodes an amino acid. In addition, one of skill will recognize many ways of generating alterations in a given nucleic acid construct. Such well-known methods include site directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well known techniques. See, Giliman and Smith (1979) *Gene* 8:81–97, Roberts et al. (1987) *Nature* 328:731–734 and Sambrook, Ausbel, Berger and Kimmel, all supra.

Modifications to nucleic acids are evaluated by routine screening techniques in suitable assays for the desired characteristic. For instance, changes in the immunological character of encoded peptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Similarly, A conservative amino acid substitutions, in one or a few amino acids in an amino acid sequence of a protein are substituted with different amino acids with highly similar properties (see, the definitions section, supra), are also readily identified as being highly similar to a disclosed construct. By conservative substitutions is meant replacing an amino acid residue with another which is biologically and/or chemically similar, e.g., one hydrophobic residue for another, or one polar residue for another. The substitutions include combinations such as, for example, Gly, Ala; Val, Ile. Leu; Asp, Glu; Asn, Gln; Ser, Thr; Lys, Arg; and Phe, Tyr. Such conservatively substituted variations of each explicitly disclosed sequence are a feature of the present invention.

D Immunogenic Conjugates

In another embodiment the present invention provides immunogenic conjugates, the immunogenic conjugates comprising an immunogenic HAV peptide covalently attached to a carrier protein. Suitable carrier proteins include, but are not limited to, the following thyroglobulin, albumins such as human serum albumin, tetanus toxoid, polyamino acids such as poly(D-lysine:D-glutamic acid), influenza, hepatitis B virus core protein, hepatitis B virus recombinant vaccine, etc.

Where the immunogenic peptide and the carrier protein are relatively short in length (i.e., less than about 50 amino acids), they are often synthesized using standard chemical peptide synthesis techniques. Where both molecules are relatively short, a chimeric molecule is optionally synthesized as a single contiguous polypeptide. Alternatively, the immunogenic peptide and the carrier molecule can be synthesized separately and then fused chemically.

Solid phase synthesis in which the C-terminal amino acid of the sequence is attached to an insoluble support followed by sequential addition of the remaining amino acids in the sequence is a preferred method for the chemical synthesis of the immunogenic conjugates of this invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis, Part A*., Merrifield, et al. *J. Am. Chem. Soc.,* 85: 2149–2156 (1963), and Stewart et al., *Solid Phase Peptide Synthesis,* 2nd ed. Pierce Chem. Co., Rockford, Ill. (1984) which are incorporated herein by reference.

In an alternative, the immunogenic conjugates of the present invention are synthesized using recombinant nucleic acid methodology. Generally, this involves creating a nucleic acid sequence that encodes the immunogenic HAV peptide-carrier protein immunogenic conjugate, placing the nucleic acid in an expression cassette under the control of a particular promoter, expressing the protein in a host, isolating the expressed protein and, if required, renaturing the protein. Techniques sufficient to guide one of skill through such procedures are found in, e.g., Berger and Kimmel, Sambrook, Ausubel, all supra.

While the immunogenic peptide and carrier molecule are often joined directly together, one of skill will appreciate that the molecules may be separated by a spacer molecule (e.g., a peptide) consisting of one or more amino acids.

Generally, the spacer will have no specific biological activity other than to join the immunogenic peptide to the carrier protein, or to preserve some minimum distance or other spatial relationship between them. However, the constituent amino acids of the spacer may be selected to influence some property of the molecule such as the folding, net charge, or hydrophobicity.

Once expressed, recombinant immunogenic conjugates can be purified according to standard procedures, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*, Academic Press, Inc. N.Y. (1990)). Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the immunogenic conjugates of the present invention may possess a conformation substantially different than the native conformations of the constituent peptides. In this case, it is often necessary to denature and reduce the polypeptide and then to cause the polypeptide to re-fold into the preferred conformation. Methods of reducing and denaturing proteins and inducing re-folding are well known to those of skill in the art (See, Debinski et al. *J. Biol. Chem.*, 268: 14065–14070 (1993); Kreitman and Pastan, *Bioconjug. Chem.*, 4: 581–585 (1993); and Buchner, et al., *Anal. Biochem.*, 205: 263–270 (1992).

E. Mosaic Proteins

In a preferred embodiment, the immunogenic peptides of the invention are combined into mosaic proteins. Typically, 2 to 20 of the immunogenic peptides are fused into a single polypeptide by recombinant or synthetic techniques.

In recombinant procedures, mosaic proteins are made by ligating synthetic or recombinant nucleic acids which encode immunogenic peptides. These nucleic acids can be ligated enzymatically (e.g., using a DNA Ligase enzyme) or synthetically. Alternatively, a single nucleic acid can be synthesized which encodes multiple immunogenic peptides. In either case, the resulting nucleic acid encodes multiple immunogenic peptides, all in the same reading frame. Thus, the translated polypeptide comprises immunogenic peptide domains.

Where the proteins are made by automated chemical synthetic procedures, concatamers of peptides can be coupled directly. This is performed chemically by joining peptides using standard chemical methods. Alternatively, a polynucleotide can be synthetically produced which encodes multiple immunogenic peptides.

Chemical or recombinant linker regions are optionally included between immunogenic peptide domains to facilitate presentation of the domains to antibodies which bind the domains. In preferred embodiments, 10–50 amino acids are inserted between immunogenic domains. Essentially any amino acid, or chemical moiety which forms amide and carboxyl linkages can be used as a linker.

F. Antibody Production

Antibodies are raised to the immunogenic HAV peptides of the present invention, including individual, allelic, strain, or species variants, and fragments thereof, both in their naturally occurring (full-length) forms and in recombinant forms. Additionally, antibodies are raised to these peptides in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

1. Antibody Production

A number of immunogens are used to produce antibodies specifically reactive with peptides. Recombinant or synthetic peptides of 10 amino acids in length, or greater, selected from sub-sequences of the immunogenic HAV peptides disclosed herein are the preferred peptide immunogen for the production of monoclonal or polyclonal antibodies. In one class of preferred embodiments, an immunogenic peptide conjugate is also included as an immunogen. Naturally occurring peptides are also used either in pure or impure form.

Recombinant peptides are expressed in eukaryotic or prokaryotic cells and purified using standard techniques. The peptide, or a synthetic version thereof, is then injected into an animal capable of producing antibodies. Either monoclonal or polyclonal antibodies can be generated for subsequent use in immunoassays to measure the presence and quantity of the peptide.

Methods of producing polyclonal antibodies are known to those of skill in the art. In brief, an immunogen, preferably a purified peptide, a peptide coupled to an appropriate carrier (e.g., GST, keyhole limpet hemanocyanin, etc.), or a peptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the peptide of interest. When appropriately high titers of antibody to the immunogen are obtained, blood is collected from the animal and antisera are prepared. Further fractionation of the antisera to enrich for antibodies reactive to the peptide is performed where desired. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference.

Antibodies, including binding fragments and single chain recombinant versions thereof, against fragments peptides are raised by immunizing animals, e.g., using immunogenic conjugates comprising a peptide fragment covalently attached (conjugated) to a carrier proteins as described above. Typically, the immunogen of interest is a peptide of at least about 3 amino acids, more typically the peptide is 5 amino acids in length, preferably, the fragment is 10 amino acids in length and more preferably the fragment is 15 amino acids in length or greater. Often, the fragment is about 20 amino acids in length. The immunogenic conjugates are typically prepared by coupling the peptide to a carrier protein (e.g., as a fusion protein) or, alternatively, they are recombinantly expressed in an immunization vector. Antigenic determinants on peptides to which antibodies bind are typically 3 to 10 amino acids in length.

Monoclonal antibodies are prepared from cells secreting the desired antibody. These antibodies are screened for binding to normal or modified peptides, or screened for agonistic or antagonistic activity, e.g., activity mediated through HAV. Specific monoclonal and polyclonal antibodies will usually bind with a $K_D$ of at least about 0.1 mM, more usually at least about 50 mM, and most preferably at least about 1 mM or better. Often, specific monoclonal antibodies bind with a $K_D$ of 0.1 mM or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen, i.e., an immunogenic HAV peptide of the present invention either alone or optionally linked to a carrier protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The peptides and antibodies of the present invention are used with or without modification, and include chimeric antibodies such as humanized murine antibodies. Other suitable techniques involve selection of libraries of recombinant antibodies in phage or similar vectors. See, Huse et al. (1989) *Science* 246: 1275–1281; and Ward, et al. (1989) *Nature* 341: 544–546.

Frequently, the peptides and antibodies will be labeled by joining, either covalently or non covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of the present invention can be used in affinity chromatography for isolating the peptides of the invention and, in addition, in isolating HAV. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified peptides are released. In addition, the antibodies can be used to screen expression libraries for particular expression products, for example, HAV proteins. Usually, the antibodies in such a procedure are labeled with a moiety allowing easy detection of presence of antigen by antibody binding. Moreover, antibodies raised against the immunogenic HAV peptides of the present invention can also be used to raise anti-idiotypic antibodies. Such antibodies are useful for detecting or diagnosing various pathological conditions related to the presence of the respective antigens.

2. Immunoassays

A particular protein can be quantified by a variety of immunoassays methods. For a review of immunological and immunoassay procedures in general, see Stites and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) Immunoassay: *A Practical Guide Academic* Press, Orlando, Fla.; Price and Newman (eds.) (1991) *Principles and Practice of Immunoassays* Stockton Press, NY; and Ngo (ed.) (1988) Non isotopic Immunoassays Plenum Press, NY.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled peptide or a labeled anti-peptide antibody. Alternatively, the labeling agent may be a third moiety, such as another antibody, that specifically binds to the antibody/peptide complex, or to a modified capture group (e.g., biotin) which is covalently linked to the peptide or anti-peptide antibody.

In a preferred embodiment, the labeling agent is an antibody that specifically binds to the capture agent. Such agents are well known to those of skill in the art, and most typically comprise labeled antibodies that specifically bind antibodies of the particular animal species from which the capture agent is derived (e.g., an anti-idiotypic antibody), or antibodies against a peptide when the peptide is the capture agent. Thus, for example, where the capture agent is a mouse derived anti-peptide antibody, the label agent may be a goat anti-mouse IgG, i.e., an antibody specific to the constant region of the mouse antibody.

Other proteins capable of specifically binding immunoglobulin constant regions, such as streptococcal protein A or protein G are also used as the labeling agent. These proteins are normal constituents of the cell walls of streptococcal bacteria. They s exhibit a strong non immunogenic reactivity with immunoglobulin constant regions from a variety of species. See, generally Kronval, et al., (1973) *J. Immunol.*, 111:1401–1406, and Akerstrom, et al., (1985) *J. Immunol.*, 135:2589–2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5EC to 45EC.

(a) Non Competitive Assay Formats

Immunoassays for detecting a peptide or an antibody to a peptide may be either competitive or noncompetitive. Non-competitive immunoassays are assays in which the amount of captured analyte (e.g., anti-peptide antibody) is directly measured. In one preferred "sandwich" assay, for example, the capture agent (e.g., immunogenic peptide antibodies) is bound directly to a solid substrate where they are immobilized. These immobilized peptides capture antibodies present in a test sample, such as blood serum. The antibody thus immobilized is then bound by a labeling agent, such as a second antibody bearing a label. Alternatively, the second antibody may lack a label, but it may, in turn, be bound by a labeled third antibody specific to antibodies of the species from which the second antibody is derived.

Sandwich assays for a peptide or antibody can also be constructed. As described above, the immobilized peptide specifically binds to the antibody present in the sample. A labeled antibody then binds to the already bound antibody. Free labeled antibody is washed away and the remaining bound labeled antibody is detected (e.g., using a gamma detector where the label is radioactive).

(b) Competitive Assay Formats

In competitive assays, the amount of analyte (e.g., immunogenic peptide or antibody to an immunogenic peptide) present in the sample is measured indirectly by measuring the amount of an added (exogenous) analyte displaced (or competed away) from a capture agent (e.g., an antibody or peptide) by the analyte present in the sample. In one competitive assay, a known amount of analyte is added to the sample and the sample is contacted with a capture agent, such as a peptide that specifically binds the analyte. The amount of analyte bound to the peptide is inversely proportional to the concentration of analyte present in the sample.

In a preferred embodiment, the capture agent is immobilized on a solid substrate. The amount of analyte bound to the capture agent is determined either by measuring the amount of antibody present in an antibody/peptide complex or, alternatively, by measuring the amount of remaining uncomplexed antibody. The amount of peptide in a sample to be assayed can also be detected by providing exogenous labeled peptide to the assay.

A hapten inhibition assay is another preferred competitive assay. In this assay, a known analyte, in this case an immunogenic peptide, is immobilized on a solid substrate. A known amount of anti-peptide antibody is added to the sample, and the sample is then contacted with the immobilized peptide. In this case, the amount of antibody bound to the immobilized marker gene polypeptide is proportional to the amount of peptide present in the sample. Again the amount of immobilized antibody is detected by quantitating either the immobilized fraction of antibody or the fraction of the antibody that remains in solution. Detection may be direct where the antibody is labeled, or indirect where a labeled moiety is subsequently added which specifically binds to the antibody as described above. One of skill will appreciate that the role of the peptide and antibody can be reversed to achieve the same effect for the quantitation of the antibody.

G. Assays for Detecting Immunogenic HAV Peptides and Antibodies To HAV

1. Sample Collection and Processing

A immunogenic peptide or, alternatively, an antibody to HAV is preferably quantified in a biological sample, such as a cell, or a tissue sample derived from a patient. Although the sample is typically taken from a human patient, the assays can be used to detect , e.g., antibodies, in samples such as sera from eukaryotes in general and, in particular, mammals, such as dogs, cats, sheep, cattle and pigs, and primates, such as humans, chimpanzees, gorillas, macaques, and baboons, and rodents such as mice, rats, and guinea pigs.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

2. Quantification of an Immunogenic Peptide or an Antibody to HAV

An immunogenic peptide or, alternatively, an antibody to HAV, can be detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion (single or double), immunoelectrophoresis, radioimmunoassays (RIAs), enzyme-linked immunosorbent assays (ELISAs), immunofluorescent assays, and the like.

3. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

4. Other Assay Formats

Western blot analysis can also be used to detect and quantify the presence of an immunogenic peptide in the sample. The technique generally comprises separating sample products by gel electrophoresis on the basis of molecular weight, transferring the separated proteins to a suitable solid support (such as a nitrocellulose filter, a nylon filter, or derivatized nylon filter), and incubating the sample with the antibodies that specifically bind immunogenic HAV peptides. The anti-peptide antibodies specifically bind to a peptide fixed on the solid support. These antibodies are directly labeled or, alternatively, they may be subsequently detected using labeled antibodies (e.g., labeled sheep anti-mouse antibodies where the antibody to a peptide is a murine antibody) that specifically bind to the anti-peptide antibody.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34–41), which is incorporated herein by reference.

5. Labels

The labeling agent can be, e.g., a peptide, a monoclonal antibody, a polyclonal antibody, an immunogenic peptide or a mosaic polypeptide of immunogenic peptides, or complex such as those described herein, or a polymer such as an affinity matrix, carbohydrate or lipid. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., LacZ, CAT, horse radish peroxidase, alkaline phosphatase and others, commonly used as detectable enzymes, either in an EIA or in an ELISA), and colorimetric labels such as colloidal gold or colored glass or plastic (e.g. polystyrene, polypropylene, latex, etc.) beads. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels are detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

6. Substrates

As mentioned above, depending upon the assay, various components, including the immunogenic HAV peptide, antipeptide antibody, or anti-idiotypic antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glassess, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, *J. Biol. Chem.* 245 3059 (1970) which are incorporated herein by reference.

H. Making Pooled Antisera for Specificity Determinations

A peptide that specifically binds to or that is specifically immunoreactive with an antibody generated against a defined immunogen, such as an immunogenic HAV peptide comprising of the amino acid sequences described herein is determined in an immunoassay. In one embodiment, the immunoassay uses a polyclonal antiserum which was raised to the immunogenic peptide. This antiserum is selected to have low crossreactivity against known peptides, and any such reactivity is removed by immunoabsorbtion prior to use in the inmmunoassay.

In order to produce antisera for use in an immunoassay, the immunogenic peptides of the invention are made and isolated as described herein. For example, recombinant protein can be produced in a mammalian or other eukaryotic cell line, or the peptides can be made synthetically. An inbred strain of mice is immunized with a selected peptide using a standard adjuvant, such as Freund's adjuvant, and a standard mouse immunization protocol (see, Harlow and Lane, supra). Alternatively, a synthetic peptide derived from the sequences disclosed herein and conjugated to a carrier protein is used as an immunogen (See, the above section relating to immunogenic conjugates).

Polyclonal sera are collected and titered against the immunogenic peptide in an immunoassay, for example, a solid phase immunoassay with the immunogen immobilized on a solid support. Polyclonal antisera with a titer of $10^4$ or greater are selected and tested for their cross reactivity against any known protein, using a competitive binding immunoassay such as the one described in Harlow and Lane, supra, at pages 570–573.

Immunoassays in the competitive binding format are used for crossreactivity determinations. For example, the immunogenic peptide is immobilized to a solid support. Proteins added to the assay compete with the binding of the antisera to the immobilized antigen. The ability of the above proteins to compete with the binding of the antisera to the immobilized protein is compared to the immunogenic peptide. The percent crossreactivity for the above proteins is calculated, using standard calculations. Those antisera with less than 10% crossreactivity with selected competitor proteins are selected and pooled. The cross-reacting antibodies are then removed from the pooled antisera by immunoabsorbtion with the competitor proteins.

The immunoabsorbed and pooled antisera are then used in a competitive binding immunoassay to compare the binding of a test peptide to the immunogenic peptide. In order to make this comparison, the two peptides are each assayed at a wide range of concentrations and the amount of each peptide required to inhibit 50% of the binding of the antisera to the immobilized is determined using standard techniques. If the amount of the test peptide required is less than twice the amount of the immunogenic peptide that is required, then the test peptide is said to specifically bind to an antibody generated to the immunogenic peptide.

As a final determination of specificity, the pooled antisera is fully immunosorbed with the immunogenic peptide against which the antisera was generated until no binding to the immunogenic peptide used in the immunosorbtion is detectable. The fully immunosorbed antisera is then tested for reactivity with the test peptide. If no reactivity is observed, then the test peptide is specifically bound by the antisera elicited by the immunogenic protein.

I. Diagnostic and Screening Assays

The immunogenic HAV peptides, antibodies and nucleic acids of the invention can be used in a number of different diagnostic applications. For instance, labeled monoclonal antibodies to polypeptides of the invention can be used to detect HAV in a biological sample. Alternatively, labelled polypeptides of the invention can be used to detect the presence of antibodies to HAV in a biological sample. For a review of the general procedures in diagnostic immunoassays, see, e.g., *Basic and Clinical Immunology* (7th Edition (D. Stites and A. Terr ed.) (1991).

More particularly, in one embodiment, the present invention provides a method of detecting the presence of antibodies against HAV in mammalian serum, the method comprising: (a) contacting an isolated, immunogenic HAV peptide of the present invention with antibodies from mammalian serum; and (b) detecting the formation of complexes between the immunogenic peptide and the antibodies. In a preferred embodiment, a number of different immunogenic HAV peptides are used in this method. A particularly preferred combination of immunogenic HAV polypeptides includes QRLKYAQEELSNEVLPPPRKMKGLF (YK-1665), (Seq. I.D. 47)

WLNPKKINLADRMLGLSGVQEIKEQ (YK-1757), (Seq. I.D. 48)

SAVAEFFQSFPSGEPSNSKLSGFFQ (YK-1832), (Seq. I.D. 65);

and conservative variations thereof.

In another embodiment, the present invention provides a method of differentiating between vaccine-induced immunity and natural HAV immunity, the method comprising: (a) contacting an isolated, nonstructural, immunogenic HAV peptide of the present invention with antibodies from mammalian serum; and (b) detecting the formation of complexes between the immunogenic peptide and the antibodies, wherein the presence of peptide-antibody complexes indicates natural HAV immunity. In a preferred embodiment, a number of different nonstructural HAV immunogenic peptides are used in this method. A particularly preferred combination of immunogenic HAV polypeptides includes QRLKYAQEELSNEVLPPPRKMKGLF (YK-1665), (Seq. I.D. 47)

WLNPKKINLADRMLGLSGVQEIKEQ (YK-1757),(Seq. I.D. 48);

SAVAEFFQSFPSGEPSNSKLSGFFQ (YK-1832), (Seq. I.D. 65);

and conservative variations thereof.

In yet another embodiment, the present invention provides a method of detecting acute phase infection, the method comprising: (a) contacting an isolated, immunogenic HAV peptide of the present invention with antibodies from mammalian serum; and (b) detecting the IgM antibodies which bind to immunogenic peptides of the present invention. The detection of IgM antibodies can be performed with a labeled secondary antibody which recognizes IgM antibodies. In a preferred embodiment, a number of different immunogenic HAV peptides are used in this method.

In a further embodiment, the present invention provides a method of detecting covalescense in a mammal, the method comprising: (a) contacting an isolated, immunogenic HAV peptide of the present invention with antibodies from mammalian serum; and (b) detecting total antibody titer by measuring binding to immunogenic peptides of the present invention. Such antibodies include, but are not limited to, IgG, IgM, IgE, and the like.

J. Pharmaceutical Compositions

The immunogenic HAV peptides of the invention are useful in therapeutic and prophylactic applications for the treatment of HAV. For instance, in one embodiment, the present invention provides a method of inducing an immune response to HAV in a mammal, the method comprising administering to the mammal an immunologically effective amount of a pharmaceutical composition comprising a pharmaceutically acceptable carrier and an isolated, immunogenic HAV peptide of the present invention. In addition, the present invention provides a method of making an antibody against HAV, the method comprising administering an immunogenic HAV peptide of the present invention to a mammal.

As such, the present invention provides immunogenic or pharmaceutical compositions, the compositions generally comprising an immunogenic HAV peptide of the present invention of the invention and a pharmaceutically acceptable carrier. Such compositions are suitable for use in a variety of drug delivery systems. Suitable formulations for use in the present invention are found in *Remington's Pharmaceutical Sciences*, Mack Publishing Company, Philadelphia, Pa., 17th ed. (1985), which is incorporated herein by reference.

For a brief review of methods for drug delivery, see, Langer, *Science* 249:1 527–1533 (1990), which is incorporated herein by reference.

The immunogenic HAV peptides of the present invention can be used in pharmaceutical and vaccine compositions that are useful for administration to mammals, particularly humans. The immunogenic peptides can be administered together in different combinations. The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The amount administered to the patient will vary depending upon what is being administered, the state of the patient and the manner of administration. In therapeutic applications, compositions are administered to a patient already suffering from HAV in an amount sufficient to inhibit spread of the virus, or at least partially arrest the symptoms of the disease and its complications. An amount adequate to accomplish this is defined as "therapeutically effective dose." Amounts effective for this use will depend on the severity of the disease, the particular composition, and the weight and general state of the patient. Generally, the dose will be in the range of about 1 mg to about 5 mg per day, preferably about 100 mg per day, for a 70 kg patient.

Alternatively, the immunogenic HAV peptides of the invention can be used prophylactically as vaccines. All of the immunogenic peptides disclosed herein can be used as vaccines. The vaccines of the invention contain as an active ingredient an immunogenically effective amount of the immunogenic HAV peptide or a combination of immunogenic HAV peptides. The immune response may include the generation of antibodies; activation of cytotoxic T lymphocytes (CTL) against cells presenting the immunogenic HAV peptides, or other mechanisms well known in the art. See, e.g., Paul *Fundamental Immunology Second Edition* published by Raven press New York, the teachings of which are incorporated herein by reference, for a description of immune response.

In a preferred embodiment, the immunogenic HAV peptides are covalently attached (conjugated) to a carrier protein as described above. Useful carrier proteins include, but are not limited to, thyroglobulin, albumins such as human serum albumin, tetanus toxoid, polyamino acids such as poly(D-lysine:D-glutamic acid), influenza, hepatitis B virus core protein, hepatitis B virus recombinant vaccine. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

In addition, DNA or RNA encoding the immunogenic HAV peptides of the present invention may be introduced into patients to obtain an immune response to the immunogenic peptides which the nucleic acid encodes. See, Wolff, et al., *Science* 247: 1465–1468 (1990) which describes the use of nucleic acids to produce expression of the immunogenic HAV peptides which the nucleic acids encode, the teachings of which are incorporated herein by reference.

Vaccine compositions containing the immunogenic HAV peptides and nucleic acids of the invention are administered to a patient to elicit a protective immune response against the polypeptide. A "protective immune response" is one which prevents or inhibits the spread of HAV and, thus, at least partially prevent the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 mg to about 1 gm of peptide for a 70 kg patient, followed boosting dosages of from about 100 mg to about 1 gm of the peptide pursuant to a If boosting regimen over weeks to months depending upon the patient's response and condition, e.g., by measuring levels of HAV in the patient's blood. For nucleic acids, typically 30–1000 mg of nucleic acid is injected into a 70 kg patient, more typically about 150–300 mg of nucleic acid is injected into a 70 kg patient followed by boosting doses as appropriate.

The invention will be described in greater detail by way of specific examples. The following examples are offered for illustrative purposes, and are intended neither to limit or define the invention in any manner.

EXAMPLES

I. Experimental Design

A. Synthetic Peptides

Peptides were synthesized by FMOC chemistry on an ACT Model MPS 350 multiple peptide synthesizer (Advanced Chemtech, Louisville, Ky.) according to the manufacturer's protocols. After characterization by amino acid analysis, high performance liquid chromatography, and capillary electrophoresis, peptides were characterized by enzyme immunoassay.

B. Sera

All anti-HAV-positive and anti-HAV-negative sera were randomly selected from a collection reposited at the Centers for Disease Control and Prevention, Atlanta, Ga. Serum specimens were collected from anti-HAV-positive patients with acute liver disease. Anti-HAV-negative serum specimens were collected from normal blood donors. All sera were initially tested by commercially available kit for the presence of anti-HAV activity (HAVAB and HAVAB-M, Abbott Laboratories, Abbott Park, Ill.)

C. EIA for Anti-HAV

Synthetic peptides (110 ml) at a concentration of 10 mg/ml in 0.1 M phosphate-buffered saline (PBS), pH 7.5, were adsorbed to microtiter wells (Immulon II, Dynatech Laboratories, Inc.) at room temperature for 12 h. Sera were diluted in PBS containing 0.1% Tween 20 and 10% normal goat serum (PBS-T) and 100 ml were added to each well, incubated for 60 min at 37E C, and washed with PBS containing Tween-20. Two different dilutions of specimen and detector antibodies were used: experiment 1 used a specimen dilution of 1:100, 100 ml of affinity purified anti-human IgG coupled to horseradish peroxidase (HRP) (Boehringer Mannheim, Indianapolis, Ind.) diluted 1:30, 000, and incubated for 1 hr and 37E C; experiment 2 used sera diluted 1:1000, 50 ml of affinity purified anti-human IgG conjugated to biotin diluted 1:8000 and 50 ml of streptavidin coupled to HRP (Boehringer Mannheim, Indianapolis, Ind.), and incubated for 30 min at 37E C. Two different cutoffs were established for experiments 1 and 2. In experiment 1, the cutoff, expressed as a P/N ratio and equal to 3.0, was statistically established as the mean of negative controls plus at least 3.5 standard deviations (SD) above the mean, where P represents the optical density value at 493 nm (OD493) of anti-HAV-positive specimens and N represents the optical density value of negative controls. In experiment 2, a different cutoff was used to ensure statistical reliability and accurate interpretation of positive results. In this case, in addition to anti-HAV-negative sera, two irrelevant synthetic peptides were used as supplemental negative controls to determine the degree of nonspecific binding of anti-HAV sera to synthetic peptides. One cutoff, expressed as a P/N ratio and equal to 3.0, corresponded to the mean of negative serum controls plus at least 3.5 SD above the mean. A second cutoff was also expressed as a P/N ratio, where P represents the optical density value at 493 nm (OD493) for HAV peptides immunoreacting with anti-HAV-positive specimens and N represents the optical density value obtained with the irrelevant peptides. The second cutoff was equal 2.0 and corresponded to the mean of OD values obtained with the irrelevant peptides plus at least 3.5 SD above the mean. Synthetic peptides were considered immunoreactive with anti-HAV serum specimens only when both cutoffs were satisfied. Tables 2–11 show P/N values obtained using the conditions for experiment 1.

II. Experimental Findings

A. Structural Proteins

Antigenic reactivity of the HAV structural proteins was extensively investigated using synthetic peptides and recombinant proteins to identify virus neutralizing antigenic epitopes. No research was conducted toward identifying diagnostically relevant antigenic epitopes within this region.

1. Structural Proteins VP4-VP2
   a. Six antigenic domains were identified within VP4-VP2 proteins,
   b. Three peptides (Nos. YK-1210, (Seq. I.D. 3), YK-1211, (Seq. I.D. 4), and YK-1216, (Seq. I.D. 7)) from 2 domains demonstrated broad immunoreactivity with IgM anti-HAV-positive sera. They reacted with more than 30.0% of anti-HAV-positive sera (range: 32.6%–56.1%). All 3 peptides contain antigenic epitopes that have not been previously reported,
   c. Peptide No. YK-1215 contains A previously reported epitope (Kulik, et al., *FEBS Letter* 367:85–88 (1995)). Additionally, this peptide contains residue Tyr that was found to be exposed on the surface of HAV particles suggesting that this region may represent an antigenically active region (Robertson, et al., supra ( )).
   d. Peptide Nos. YK-1206, (Seq. I.D. 1), YK-1210, (Seq. I.D. 3), YK-1211, (Seq. I.D. 4), and YK-1216, (Seq. I.D. 7) from 3 antigenic domains demonstrated strong immunoreactivity with IgM anti-HAV-positive sera. Some of the anti-HAV-positive sera were found to immunoreact with these peptides with P/N values greater than 10.0.
2. Structural Protein VP3
   a. Six antigenic domains were identified within VP3 protein,
   b. Four peptides (Nos. YK-1236, (Seq. I.D. 12), YK-1249, (Seq. I.D. 19), YK-1250, (Seq. I.D. 20) and YK-1261. (Seq. I.D. 22)) that belong to 3 antigenic domains were very broadly immunoreactive. These peptides demonstrated immunoreactivity with more than 30.0% of IgM anti-HAV-positive sera (range: 37.0–47.8%). Peptide No. YK-1236, (Seq. I.D. 12) contains an antigenic epitope that was previously reported (Kulik, et al., supra (1995)). Very weakly reactive peptides (Nos. YK-1241, (Seq. I.D. 13), YK-1242, (Seq. I.D. 14), and YK-1243, (Seq. I.D. 15)) contain residues Asp315 and Gln319 that were found to be essential parts of the HAV major conformational neutralizing epitope (Lemon, et al., *Virology* 188:285–295 (1992)). These peptides also contain the region at position 308–321 known to elicit antibody that recognizes natural HAV particles,
   c. Peptide Nos. YK-1250, (Seq. I.D. 20), and YK-1252, (Seq. I.D. 21), are partially overlapped with an antigenic epitope identified by Kulik, et al., supra (1995). However, Peptide Nos. YK-1250, (Seq. I.D. 20) and YK-1252, (Seq. I.D. 21), do not appear to model this epitope because neither peptide contains the complete sequence of this epitope. In addition, Peptide No. YK-1215, (Seq. I.D. 6) containing the epitope identified by Kulik, et al., supra (1995) was not found immunoreactive.
   d. Peptide Nos. YK-1249, (Seq. I.D. 19), YK-1250, (Seq. I.D. 20), and YK-1261, (Seq. I.D. 22) contain at least 2 broadly and strongly immunoreactive antigenic regions that have considerable diagnostic significance. Antigenic reactivity of these regions have not been previously identified.
3. Structural Protein VP1
   a. Nine antigenic domains were identified within VP1 protein, b. Five peptides (Nos. YK-1266, (Seq. I.D. 24), YK-1273, (Seq. I.D. 28), YK-1276, (Seq. I.D. 30), YK-1313, (Seq. I.D. 37), and YK-1314, (Seq. I.D. 38)) from 4 antigenic domains were found broadly reactive with immunoreactivity to more than 30.0% of IgM anti-HAV-positive sera (range: 30.4–54.2%), c. Ten peptides (Nos. YK-1265, (Seq. I.D. 23), YK-1266, (Seq. I.d. 24), YK-1268, (Seq. I.D. 25), YK-1272, (Seq. I.D. 27), YK-1273, (Seq. I.D. 28), YK-1274, (Seq. I.D. 29), YK-1307, (Seq. I.D. 33), YK-1312, (Seq. I.D. 36), YK-1313, (Seq. I.D. 37), and YK-1314, (Seq. I.D. 38)) demonstrated strong antibody binding with a mean P/N ratio greater than 5.0, d. Peptide Nos. YK-1265, (Seq. I.D. 23) and YK-1266, (Seq. I.D. 24) contain the sequence of antigenic epitope that has been previously found to elicit neutralizing antibody (Emini, et al., *J. Virol.* 55:836–839 (1985); Lemon, et al., supra (1992)).

e. Peptide No. YK-1279, (Seq. I.D. 31) contains Ser102 and Peptide No. YK-1290; (Seq: I.D. 32) contains Val171 and Ala176, which were previously found to be important for the functional activity of the major HAV neutralizing antigenic epitope, f. Peptide Nos. YK-1307, (Seq. I.D. 33) and YK-1308, (Seq. I.D. 34) are located within the region at position 714–752 aa that was found exposed on the surface of HAV particles (Robertson, et al., *Arch. Virol.* 104:117–128 (1989)). Surface exposure is generally considered to be an important indicator of potential antigenic reactivity, g. Peptide Nos. YK-1273, (Seq. I.D. 28), YK-1276, (Seq. I.D. 30), YK-1313, (Seq. I.D. 37) and YK-1314, (Seq. I.D. 38) belong to 3 antigenic domains. These peptides demonstrated broad and strong antigenic reactivity that suggests they have significant diagnostic relevance. The regions spanned with these 4 peptides have never been reported as antigenically active sites literature.

B. Nonstructural Proteins

The antigenic composition of the entire HAV nonstructural region has never been previously reported. Only 2 groups have published experimental results indicating the immunologic reactivity of the HAV nonstructural proteins (Robertson, et al., supra (1992)). However, no attempt was made to identify the antigenic composition of these proteins.

2. Nonstructural Protein P2A a. Three antigenic domains were identified within the P2A protein, b. Five peptides (Nos. YK-1315, (Seq. I.D. 39), YK-1316, (Seq. I.D. 40), YK-1317, (Seq. I.D. 41), YK-1318, (Seq. I.D. 42), and YK-1327, (Seq. I.D. 44)) from 2 domains were found immunoreactive with more than 30.0% of IgM anti-HAV-positive sera (range: 31.3–83.3%), c. Six peptides (Nos. YK-1315, (Seq. I.D. 39), YK-1316, (Seq. I.D. 40), YK-1317, (Seq. I.D. 41), YK-1318, (Seq. I.D. 42), YK-1327, (Seq. I.D. 44) and YK-1331, (Seq. I.D. 46)) immunoreacted with anti-HAV-positive sera with the mean P/N ratio greater than 5.0, d. Peptide No. YK-1317, (Seq. I.D. 41) models the most immunoreactive epitope(s) identified in this study. Additional sets of overlapping 12- and 25-mer peptides were prepared from within the region spanned with peptides YK-1315, (Seq. I.D. 39)-YK-1319, (Seq. I.D. 43). One 25-mer peptide (No. YK-1665, (Seq. I.D. 47) with the sequence QRLKYAQEELSNEVLPPPRKMKGLF, which includes the entire sequence of Peptide No. YK-1317, (Seq. I.D. 41), was found to have a greater immunoreactivity than Peptide No. YK-1317, (Seq. I.D. 41). Peptide No. YK-1665, (Seq. I.D. 47) reacted with more than 95.0% of IgM anti-HAV-positive sera.

e. Analysis of additional sets of overlapping 12- and 25-mer peptides prepared from within the region spanned with Peptide Nos. YK-1327, (Seq. I.D. 44), YK-1328, (Seq. I.D. 45), and YK-1331, (Seq. I.D. 46), allowed for the identification of another very strong antigenically reactive peptide (No. YK-1757, (Seq. I.D. 48)) containing the sequence WLNPKKINLADRMLGLSGVQEIKEQ. Peptide No. YK-1757, (Seq. I.D. 48) contains the complete sequence of Peptide No. YK-1331, (Seq. I.D. 46). This new peptide was found to immunoreact with more than 95.0% of IgM anti-HAV-positive sera, f. Peptide Nos. YK-1665, (Seq. I.D. 47) and YK-1757, (Seq. I.D. 48) are the two most immunoreactive peptides identified in this study. We found that the combination of these two peptides is sufficient to detect 100.0% of acute HAV infections.

2. Nonstructural Protein P2B a. Only one peptide (No. YK-1334, (Seq. I.D. 49)) derived from the P2B protein was found marginally immunoreactive.

3. Nonstructural Protein P2C a. Six antigenic domains were identified within the HAV protein P2C, b. No single peptide immunoreacted with more than 30.0% of anti-HAV-positive sera. The most broadly reactive peptides were Nos. YK-1347, (Seq. I.D. 51), YK-1348, (Seq. I.D. 52), and YK-1367, (Seq. I.D. 61), which demonstrated immunoreactivity with 27.1%, 29.2% and 22.0%, respectively, c. Six peptides from 5 antigenic domains showed strong immunoreactivity with a mean P/N ratio greater than 5.0, d. Peptide Nos. YK-1347, (Seq. I.D. 51), YK-1348, (Seq. I.D. 52), and YK-1367, (Seq. I.D. 61) are the most diagnostically pertinent peptides found within this region.

4. Nonstructural Protein P3A a. Only one antigenic domain was found within this region, All 3 immunoreactive peptides derived from this protein showed strong antigenic reactivity with a mean P/N value greater than 5.0, b. Peptide Nos. YK-1368, (Seq. I.D. 62) and YK-1369, (Seq. I.D. 63) were found very broadly reactive. Each peptide reacted with more than 50.0% of anti-HAV-positive sera, c. Additional sets of 12- and 20-mer overlapping peptides were prepared for the region spanned with peptide Nos. YK-1368, (Seq. I.D. 62)-YK-1370, (Seq. I.D. 64). One 25-mer peptide (No. YK-1832, (Seq. I.D. 65) with the sequence SAVAEFFQSFPSGEPSNSKLSGFFQ was found to immunoreact with about 86.0% of anti-HAV-positive sera. Peptide No. YK-1832, (Seq. I.D. 65) contains 19 aa residues found within Peptide Nos. YK-1369, (Seq. I.D. 63) and YK-1370, (Seq. I.D. 64). This 25-mer peptide is one of 3 the most immunoreactive peptides identified in this study (Nos. YK-1665, (Seq. I.D. 47), YK-1757, (Seq. I.D. 48), and YK-1832, (Seq. I.D. 65)).

4. Nonstructural Protein P3B
   a. The protein is only 23 aa long. Only one peptide, YK-1374, (Seq. I.D. 66), was prepared from this protein. This peptide demonstrated very broad and strong antigenic reactivity and can be considered as one of the most diagnostically relevant peptides identified in this study.
5. Nonstructural Protein P3C
   a. Four antigenic domains were identified within this region,
   b. Five out of 6 immunoreactive peptides were strongly immunoreactive with a mean P/N value greater than 6.62,
   c. Only one peptide (No. YK-1393), (Seq. I.D. 72) demonstrated very broad and strong antigenic reactivity. This peptide reacted with 58.5% of tested anti-HAV-positive sera with a mean P/N value 10.15. This peptide should be considered as another very important diagnostic reagent.
6. Nonstructural Protein P3D
   a. Nine antigenic domains were identified within this region,
   b. Twelve peptides demonstrated strong antigenic reactivity with a mean P/N ratio greater than 5.0,
   c. Only Peptide No. YK-1394, (Seq. I.D. 73) was found to be reactive with more than 30.0% of anti-HAV-positive sera. This peptide should be considered as a candidate for the development of HAV diagnostic tests systems.

III. New Broadly and Strongly Immunoreactive Regions of Diagnostic Importance Identified with Synthetic Peptides
   A. Structural proteins
      Region 1: Peptide Nos. YK-1210, (Seq. I.D. 3, YK-1211, (Seq. I.D. 4)
      Region 2: Peptide No. YK-1216, (Seq. I.D. 7)
      Region 3: Peptide Nos. YK-1249, (Seq. I.D. 19), YK-1250, (Seq. I.D. 20)
      Region 4: Peptide No. YK-1261, (Seq. I.D. 22)
      Region 5: Peptide No. YK-1273, (Seq. I.D. 28)
      Region 6: Peptide No. YK-1276, (Seq. I.D. 30)
      Region 7: Peptide No. YK-1313, (Seq. I.D. 37), YK-1314, (Seq. I.D. 38)
   B. Nonstructural proteins
      Region 8: Peptide Nos. YK-1315, (Seq. I.D. 39), YK-1316, (Seq. I.D. 40), YK-1317, (Seq. I.D. 41), YK-1318, (Seq. I.D. 42) YK-1665, (Seq. I.D. 47) (analog of YK-1317, (Seq. I.D. 41))
      Region 9: Peptide No. YK-1327, (Seq. I.D. 44)
      Region 10: Peptide No. YK-1757, (Seq. I.D. 48) (analog of YK-1331, (Seq. I.D. 46))
      Region 11: Peptide Nos. YK-1368, (Seq. I.D. 62), YK-1369, (Seq. I.D. 63), YK-1832, (Seq. I.D. 65) (analog of YK-1369, (Seq. I.D. 63) and YK-1370, (Seq. I.D. 64))
      Region 12: Peptide No. YK-1374, (Seq. I.D. 66)
      Region 13: Peptide No. YK-1393, (Seq. I.D. 72)
      Region 14: Peptide No. YK-1394, (Seq. I.D. 73)
IV. Tables

TABLE 2

ANTIGENIC REACTIVITY OF SYNTHETIC PEPTIDES DERIVED FROM THE VP4 (1–23 aa) AND VP2 (24–245 aa) PROTEINS OF HEPATITIS A VIRUS

| Peptide | Sequence | Localization, aa | Reactivity with acute sera | P/N for acute sera | Reactivity with negative sera |
|---|---|---|---|---|---|
| YK-1206 | GLDHILSLADIEEEQMIQSV | 15–34 | 8/42 | 9.46 | 0/46 |
| | Seq. I.D. 1 | | 19.1% | (3.01–27.07) | |
| YK-1208 | DRTAVTGASYFTSVDQSSVH | 35–54 | 5/41 | 4.29 | 0/46 |
| | Seq. I.D. 2 | | 12.2% | (3.27–5.54) | |
| YK-1210 | EVGSHQVEPLRTSVDKPGSK | 57–76 | 15/46 | 7.31 | 0/48 |
| | Seq. I.D. 3 | | 32.6% | (3.93–20.47) | |
| YK-1211 | EPLRTSVDKPGSKKTQGEKF | 64–83 | 21/46 | 9.33 | 0/48 |
| | Seq. I.D. 4 | | 45.7% | (3.37–27.92) | |
| YK-1212 | DKPGSKKTQGEKFFLIHSAD | 71–90 | 3/41 | 3.5 | 0/46 |
| | Seq. I.D. 5 | | 7.3% | (3.04–3.96) | |
| YK-1215* | LYNEQFAVQGLLRYHTYARF | 110–129 | 10/41 | 5.29 | 0/46 |
| | Seq. I.D. 6 | | 24.4% | (3.41–8.83) | |
| YK-1216* | HTYARFGIEIQVQINPTPFQ | 124–143 | 23/41 | 5.3 | 4/46 |
| | Seq. I.D. 7 | | 56.1% | (3.42–10.79) | |
| YK-1217 | INPTPFQQGGLICAMVPGDQ | 137–156 | 4/41 | 4.03 | 0/46 |
| | Seq. I.D. 8 | | 9.8% | (3.94–4.12) | |
| YK-1222 | HFKDPQYPVWELTIRVWSEL | 194–213 | 2/41 | 4.29 | 0/46 |
| | Seq. I.D. 9 | | 4.9% | | |
| YK-1224 | NIGTGTSAYTSLNVLARFTD | 214–233 | 9/41 | 3.53 | 0/46 |
| | Seq. I.D. 10 | | 22.0% | (3.09–4.17) | |

*background reactivity with anti-HAV-negative serum specimens is twice higher than for other peptides

TABLE 3

ANTIGENIC REACTIVITY OF SYNTHETIC PEPTIDES DERIVED FROM THE VP3 PROTEIN (246–491 aa) OF HEPATITIS A VIRUS

| Peptide | Sequence | Localization, aa | Reactivity with acute sera | P/N for acute sera | Reactivity with negative sera |
| --- | --- | --- | --- | --- | --- |
| YK-1235 | SDPSQGGGIKITHFTTWTSI Seq. I.D. 11 | 283–302 | 11/46 23.9% | 4.2 (3.0–4.95) | 0/48 |
| YK-1236 | GGIKITHFTTWTSIPTLAAQ Seq. I.D. 12 | 289–308 | 22/46 47.8% | 4.68 (3.1–9.33) | 0/48 |
| YK-1241 | QFPFNASDSVGQQIKVIPVD Seq. I.D. 13 | 308–327 | 1/41 2.4% | 3.56 | 0/46 |
| YK-1242 | FNASDSVGQQIKVIPVDPYF Seq. I.D. 14 | 311–330 | 1/41 2.4% | 3.1 | 0/46 |
| YK-1243 | SDSVGQQIKVIPVDPYFFQM Seq. I.D. 15 | 314–333 | 1/41 2.4% | 3.47 | 0/46 |
| YK-1244 | IKVIPVDPYFFQMTNTNPDQ Seq. I.D. 16 | 321–340 | 6/41 14.6% | 4.2 (3.55–5.2) | 0/46 |
| YK-1247 | KCITALASICQMFCFWRGDL Seq. I.D. 17 | 341–360 | 9/46 19.6% | 3.96 (3.06–4.49) | 0/48 |
| YK-1248 | FWRGDLVFDFQVFPTKYHSG Seq. I.D. 18 | 355–374 | 3/41 7.3% | 3.16; 3.2 | 0/46 |
| YK-1249* | FDFQVFPTKYHSGRLLFCFV Seq. I.D. 19 | 362–381 | 18/46 39.1% | 5.03 (3.07–7.03) | 0/48 |
| YK-1250* | FPTKYHSGRLLFCFVPGNEL Seq. I.D. 20 | 367–386 | 17/46 37.0% | 5.68 (3.4–7.92) | 0/48 |
| YK-1252 | GITLKQATTAPCAVMDITGV Seq. I.D. 21 | 391–410 | 2/41 4.9% | 3.67; 17.95 | 0/46 |
| YK-1261* | VASHVRVNVYLSAINLECFA Seq. I.D. 22 | 461–480 | 16/41 39.0% | 5.27 (3.72–7.9) | 1/46 |

*background reactivity with anti-HAV-negative serum specimens is twice higher than for other peptides

TABLE 4

ANTIGENIC REACTIVITY OF SYNTHETIC PEPTIDES DERIVED FROM THE VP1 PROTEIN (492–791 aa) OF HEPATITIS A VIRUS

| Peptide | Sequence | Localization, aa | Reactivity with acute sera | P/N for acute sera | Reactivity with negative sera |
| --- | --- | --- | --- | --- | --- |
| YK-1265 | TTVSTEQNVPDPQVGITTMK Seq. I.D. 23 | 501–520 | 9/41 22.0% | 6.7 (3.23–9.57) | 0/46 |
| YK-1266 | QNVPDPQVGITTMKDLKGKA Seq. I.D. 24 | 507–526 | 14/46 30.4% | 8.25 (3.27–18.30) | 0/48 |
| YK-1268 | NRGKMDVSGVQAPVGAITTI Seq. I.D. 25 | 527–546 | 7/46 15.2% | 9.1 (6.07–15.25) | 2/48 |
| YK-1271 | ITTIEDPVLAKKVPETFPEL Seq. I.D. 26 | 543–562 | 4/41 9.8% | 4.97 (3.33–7.76) | 1/46 |
| YK-1272 | EDPVLAKKVPETFPELKPGE Seq. I.D. 27 | 547–566 | 6/41 14.6% | 5.4 (4.87–6.12) | 1/46 |
| YK-1273* | AKKVPETFPELKPGESRHTS Seq. I.D. 28 | 552–571 | 19/46 41.3% | 5.15 (3.15–8.58) | 3/48 |
| YK-1274 | FPELKPGESRHTSDHMSIYK Seq. I.D. 29 | 559–578 | 9/46 19.6% | 5.31 (3.0–8.47) | 1/48 |
| YK-1276* | DHMSIYKFMGRSHFLCTFTF Seq. I.D. 30 | 572–591 | 17/41 41.5% | 4.38 (3.15–5.62) | 0/46 |
| YK-1279 | HFLCTFTFNSNNKEYTFPIT Seq. I.D. 31 | 584–603 | 7/41 17.1% | 3.43 (3.11–3.67) | 1/46 |
| YK-1290 | TPVGLAVDTPWVEKESALSI Seq. I.D. 32 | 651–670 | 6/48 12.5% | 4.48 (3.0–6.44) | 1/51 |
| YK-1307 | LSFSCYLSVTEQSEFYFPRA Seq. I.D. 33 | 734–753 | 6/48 12.5% | 5.88 (4.17–7.64) | 0/51 |
| YK-1308 | SVTEQSEFYFPRAPLNSNAM Seq. I.D. 34 | 741–760 | 1/48 2.1% | 3.32 | 0/51 |
| YK-1310 | PLNSNAMLSTESMMSRIAAG Seq. I.D. 35 | 754–773 | 3/48 6.3% | 3.68; 5.23 | 0/51 |
| YK-1312 | MSRIAAGDLESSVDDPRSEE Seq. I.D. 36 | 767–786 | 13/48 27.1% | 8.7 (4.44–25.9) | 2/51 |

TABLE 4-continued

ANTIGENIC REACTIVITY OF SYNTHETIC PEPTIDES DERIVED FROM THE VP1 PROTEIN (492–791 aa) OF HEPATITIS A VIRUS

| Peptide | Sequence | Localization, aa | Reactivity with acute sera | P/N for acute sera | Reactivity with negative sera |
|---|---|---|---|---|---|
| YK-1313 | AGDLESSVDDPRSEEDKRFE Seq. I.D. 37 | 772–791 | 18/48 37.5% | 15.79 (3.0–108.06) | 3/51 |
| YK-1314 | VDDPRSEEDKRFESHIECRK Seq. I.D. 38 | 779–798 | 26/48 54.2% | 14.68 (3.53–89.96) | 1/51 |

*background reactivity with anti-HAV-negative serum specimens is twice higher than for other peptides

TABLE 5

ANTIGENIC REACTIVITY OF SYNTHETIC PEPTIDES DERIVED FROM THE P2A PROTEIN (792–980 aa) OF HEPATITIS A VIRUS

| Peptide | Sequence | Localization, aa | Reactivity with acute sera | P/N for acute sera | Reactivity with negative sera |
|---|---|---|---|---|---|
| YK-1315 | SHIECRKPYKELRLEVGKQR Seq. I.D. 39 | 792–811 | 26/48 54.2% | 13.71 (3.1–75.61) | 1/51 |
| YK-1316 | PYKELRLEVGKQRLKYAQEE Seq. I.D. 40 | 799–818 | 20/48 41.7% | 8.71 (3.5–17.8) | 2/51 |
| YK-1317 | QRLKYAQEELSNEVLPPPRK Seq. I.D. 41 | 810–829 | 55/66 83.3% | 19.35 (3.47–125.8) | 1/66 |
| YK-1318 | VLPPPRKMKGLFSQAKISLF Seq. I.D. 42 | 823–842 | 15/48 31.3% | 5.94 (3.4–8.68) | 0/51 |
| YK-1319* | FSQAKISLFYTEEHEIMKFS Seq. I.D. 43 | 834–853 | 13/48 27.1% | 3.87 (3.14–5.01) | 2/51 |
| YK-1327 | KVNFPHGMLDLEEIAANSKD Seq. I.D. 44 | 922–941 | 15/48 31.3% | 6.16 (3.28–9.76) | 1/51 |
| YK-1328 | DLEEIAANSKDFPNMSETDL Seq. I.D. 45 | 931–950 | 6/48 12.5% | 4.76 (3.74–6.39) | 1/51 |
| YK-1331 | KINLADRMLGLSGVQEIKEQ Seq. I.D. 46 | 961–980 | 13/48 27.1% | 5.71 (3.71–10.3) | 0/51 |

*background reactivity with anti-HAV-negative serum specimens is twice higher than for other peptides

TABLE 6

ANTIGENIC REACTIVITY OF SYNTHETIC PEPTIDES DERIVED FROM THE P2B PROTEIN (981–1087 aa) OF HEPATITIS A VIRUS

| Peptide | Sequence | Localization, aa | Reactivity with acute sera | P/N for acute sera | Reactivity with negative sera |
|---|---|---|---|---|---|
| YK-1334 | VIQQLNQDEHSHIIGLLRVM Seq. I.D. 49 | 1030–1049 | 5/48 10.4% | 4.27 (3.16–5.27) | 2/51 |

TABLE 7

ANTIGENIC REACTIVITY OF SYNTHETIC PEPTIDES DERIVED FROM THE P2C PROTEIN (1088–1422 aa) OF HEPATITIS A VIRUS

| Peptide | Sequence | Localization, aa | Reactivity with acute sera | P/N for acute sera | Reactivity with negative sera |
|---|---|---|---|---|---|
| YK-1341 | NILKDNQQKIEKAIEEADEF Seq. I.D. 50 | 1133–1152 | 3/48 6.3% | 5.23 (3.44–8.26) | 1/51 |
| YK-1347 | LGSINQAMVTRCEPVVCYLY Seq. I.D. 51 | 1210–1229 | 13/48 27.1% | 4.16 (3.18–6.2) | 2/51 |
| YK-1348 | RCEPVVCYLYGKRGGGKSLT Seq. I.D. 52 | 1220–1239 | 14/48 29.2% | 6.96 (3.66–15.48) | 2/51 |
| YK-1352 | TKPVASDYWDGYSGQLVCII Seq. I.D. 53 | 1261–1280 | 8/48 16.7% | 4.45 (3.38–5.81) | 0/51 |

TABLE 7-continued

ANTIGENIC REACTIVITY OF SYNTHETIC PEPTIDES DERIVED FROM THE P2C PROTEIN (1088–1422 aa) OF HEPATITIS A VIRUS

| Peptide | Sequence | Localization, aa | Reactivity with acute sera | P/N for acute sera | Reactivity with negative sera |
|---|---|---|---|---|---|
| YK-1356 | VSGCPMRLNMASLEEKGRHF Seq. I.D. 54 | 1299–1318 | 8/48 16.7% | 5.49 (3.36–10.96) | 0/51 |
| YK-1357 | LNMASLEEKGRHFSSPFIIA Seq. I.D. 55 | 1306–1325 | 4/48 8.3% | 4.49 (4.06–4.85) | 1/51 |
| YK-1360 | NPSPKTVYVKEAIDRRLHFK Seq. I.D. 56 | 1331–1350 | 4/41 9.8% | 4.08 (3.68–4.71) | 0/46 |
| YK-1361 | VKEAIDRRLHFKVEVKPASF Seq. I.D. 57 | 1339–1358 | 5/41 12.2% | 4.12 (3.21–6.28) | 0/46 |
| YK-1362 | VKPASFFKNPHNDMLNVNLA Seq. I.D. 58 | 1353–1372 | 6/41 14.6% | 7.82 (3.4–18.05) | 0/41 |
| YK-1363 | KNPHNDMLNVNLAKTNDAIK Seq. I.D. 59 | 1360–1379 | 5/41 12.2% | 5.96 (5.31–6.33) | 0/41 |
| YK-1364 | LAKTNDAIKDMSCVDLIMDG Seq. I.D. 60 | 1371–1390 | 4/41 9.8% | 4.9 (3.5–6.18) | 1/41 |
| YK-1367 | VMTVEIRKQNMTEFMELWSQ Seq. I.D. 61 | 1403–1422 | 9/41 22.0% | 7.82 (4.18–16.26) | 1/41 |

TABLE 8

ANTIGENIC REACTIVITY OF SYNTHETIC PEPTIDES DERIVED FROM THE P3A PROTEIN (1423–1496 aa) OF HEPATITIS A VIRUS

| Peptide | Sequence | Localization, aa | Reactivity with acute sera | P/N for acute sera | Reactivity with negative sera |
|---|---|---|---|---|---|
| YK-1368 | SQGISDDDNDSAVAEFFQSF Seq. I.D. 62 | 1421–1440 | 26/41 63.4% | 9.58 (4.27–19.82) | 1/27 |
| YK-1369 | DSAVAEFFQSFPSGEPSNSK Seq. I.D. 63 | 1430–1449 | 24/41 58.5% | 21.71 (3.8–42.62) | 1/27 |
| YK-1370 | FQSFPSGEPSNSKLSGFFQS Seq. I.D. 64 | 1437–1456 | 10/41 24.4% | 8.05 (3.05–18.48) | 1/27 |

TABLE 9

ANTIGENIC REACTIVITY OF SYNTHETIC PEPTIDES DERIVED FROM THE P3B PROTEIN (1497–1519 aa) OF HEPATITIS A VIRUS

| Peptide | Sequence | Localization, aa | Reactivity with acute sera | P/N for acute sera | Reactivity with negative sera |
|---|---|---|---|---|---|
| YK-1374 | HGVTKPKQVIKLDADPVESQ Seq. I.D. 66 | 1500–1519 | 18/41 43.9% | 10.57 (3.28–29.07) | 0/27 |

TABLE 10

ANTIGENIC REACTIVITY OF SYNTHETIC PEPTIDES DERIVED FROM THE P3C PROTEIN (1520–1738 aa) OF HEPATITIS A VIRUS

| Peptide | Sequence | Localization, aa | Reactivity with acute sera | P/N for acute sera | Reactivity with negative sera |
|---|---|---|---|---|---|
| YK-1376 | GLVRKNLVQFGVGEKNGCVR Seq. I.D. 67 | 1526–1545 | 3/41 7.3% | 6.71 (3.8–12.77) | 0/27 |
| YK-1382 | DVVLMKVPTIPKFRDITQHF Seq. I.D. 65 | 1603–1622 | 1/41 2.4% | 8.4 | 0/27 |
| YK-1388 | MEEKATYVHKKNDGTTVDLT Seq. I.D. 70 | 1656–1675 | 4/41 9.8% | 4.29 (3.99–4.7) | 0/27 |
| YK-1389 | KNDGTTVDLTVDQAWRGKGE Seq. I.D. 70 | 1666–1685 | 3/41 7.3% | 10.33 (5.53–18.26) | 0/27 |

TABLE 10-continued

ANTIGENIC REACTIVITY OF SYNTHETIC PEPTIDES
DERIVED FROM THE P3C PROTEIN (1520–1738 aa) OF
HEPATITIS A VIRUS

| Peptide | Sequence | Localization, aa | Reactivity with acute sera | P/N for acute sera | Reactivity with negative sera |
|---|---|---|---|---|---|
| YK-1390 | RGKGEGLPGMCGGALVSSNQ Seq. I.D. 71 | 1681–1700 | 10/41 24.4% | 6.62 (3.52–13.98) | 1/27 |
| YK-1393 | VAKLVTQEMFQNIDKKIESQ Seq. I.D 72 | 1719–1738 | 24/41 58.5% | 10.15 (4.64–16.36) | 1/27 |

TABLE 11

ANTIGENIC REACTIVITY OF SYNTHETIC PEPTIDES
DERIVED FROM THE P2C PROTEIN (1088–1422 aa) OF
HEPATITIS A VIRUS

| Peptide | Sequence | Localization, aa | Reactivity with acute sera | P/N for acute sera | Reactivity with negative sera |
|---|---|---|---|---|---|
| YK-1394 | RIMKVEFTQCSMNVVSKTLF Seq. I.D. 73 | 1739–1758 | 13/41 31.7% | 6.98 (4.05–12.93) | 3/27 |
| YK-1395 | FTQCSMNVVSKTLFRKSPIY Seq. I.D. 74 | 1745–1764 | 8/41 19.5% | 6.52 (3.51–17.52) | 1/27 |
| YK-1399 | MLSKYSLPIVEEPEDYKEAS Seq. I.D. 76 | 1791–1810 | 5/41 12.2% | 6.86 (4.05–16.46) | 1/27 |
| YK-1407 | LDENGLLLGVHPRLAQRILF Seq. I.D. 76 | 1866–1885 | 2/41 4.9% | 3.43; 3.98 | 0/27 |
| YK-1411 | CPKDELRPLEKVLESKTRAI Seq. I.D. 77 | 1903–1922 | 8/41 19.5% | 8.18 (4.65–17.65) | 0/27 |
| YK-1412 | SKTRAIDACPLDYSILCRMY Seq. I.D. 78 | 1917–1936 | 10/41 24.4% | 6.04 (3.4–15.15) | 2/27 |
| YK-1414 | RMYWGPAISYFHLNPGFHTG Seq. I.D. 79 | 1934–1953 | 1/41 2.4% | 3.35 | 0/27 |
| YK-1418 | KTMIRFGDVGLDLDFSAFDA Seq. I.D. 80 | 1969–1988 | 6/41 14.6% | 4.5 (3.35–6.21) | 1/27 |
| YK-1419 | DLDFSAFDASLSPFMIREAG Seq. I.D. 81 | 1980–1999 | 5/41 12.2% | 5.27 (3.98–8.49) | 1/27 |
| YK-1424 | INNVNLYYVFSKIFGKSPVF Seq. I.D. 82 | 2052–2071 | 3/41 7.3% | 6.69 (3.48–10.83) | 0/27 |
| YK-1428 | GQKIVDEFKKLGMTATSADK Seq. I.D. 83 | 2102–2121 | 1/41 2.4% | 7.28 | 0/27 |
| YK-1429 | LGMTATSADKNVPQLKPVSE Seq. I.D. 84 | 2112–2131 | 5/41 12.2% | 10.25 (4.92–27.38) | 0/27 |
| YK-1431 | PQLKPVSELTFLKRSFNLVE Seq. I.D. 85 | 2124–2143 | 4/41 9.8% | 14.13 (3.17–27.53) | 1/27 |
| YK-1434 | SEKITWSLIAWQRSNAEFEQ Seq. I.D. 86 | 2151–2170 | 11/41 26.8% | 7.47 (3.85–16.03) | 1/27 |
| YK-1435 | SLIAWQRSNAEFEQNLENAQ Seq. I.D. 87 | 2157–2176 | 6/41 14.6% | 8.96 (5.16–13.71) | 1/27 |
| YK-1436 | WQRSNAEFEQNLENAQWFAF Seq. I.D. 88 | 2161–2180 | 4/41 9.8% | 4.49 (3.35–5.89) | 1/27 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method of detecting the presence of antibodies against HAV in mammalian serum, said method comprising:

(a) contacting one or more isolated, immunogenic HAV peptides with antibodies from mammalian serum, wherein the immunogenic peptides comprise an amino acid sequence selected from the group consisting of SEQ ID NOS: 1–72 and conservative variations thereof, and (b) detecting the formation of complexes between the immunogenic peptides and the antibodies.

2. The method of claim 1, wherein the immunogenic peptide has the amino acid sequence of SEQ ID NO: 47 and conservative variations thereof.

3. An isolated, antigenic hepatitis A virus peptide consisting of the amino acid sequence identified as SEQ ID NO:42.

4. An isolated, antigenic hepatitis A virus peptide consisting of the amino acid sequence identified as SEQ ID NO:43.

5. An isolated, antigenic hepatitis A virus peptide consisting of the amino acid sequence identified as SEQ ID NO:44.

6. An isolated, antigenic hepatitis A virus peptide consisting of the amino acid sequence identified as SEQ ID NO:45.

7. An isolated, antigenic hepatitis A virus peptide consisting of the amino acid sequence identified as SEQ ID NO:46.

8. An isolated, antigenic hepatitis A virus HAV peptide consisting of the amino acid sequence identified as SEQ ID NO:47.

9. An isolated, antigenic hepatitis A virus HAV peptide consisting of the amino acid sequence identified as SEQ ID NO:48.

* * * * *

SEQUENCE LISTING (1) GENERAL INFORMATION:

(iii) NUMBER OF SEQUENCES: 88

```
(2) INFORMATION FOR SEQ ID NO:1:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1206

(xi) SEQUENCE DESCRIPTION: SEQ ID NO:1:

Gly Leu Asp His Ile Leu Ser Leu Ala Asp Ile Glu Glu Glu Gln Met
1               5                  10                  15

Ile Gln Ser Val
        20

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1208

(xi) SEQUENCE DESCRIPTION: SEQ ID NO:2:

Asp Arg Thr Ala Val Thr Gly Ala Ser Tyr Phe Thr Ser Val Asp Gln
1               5                  10                  15

Ser Ser Val His
        20

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
```

```
            (B) LOCATION: 1..20
            (D) OTHER INFORMATION: /label= YK-1210

(xi) SEQUENCE DESCRIPTION: SEQ ID NO:3:

Glu Val Gly Ser His Gln Val Glu Pro Leu Arg Thr Ser Val Asp Lys
1               5                  10                  15

Pro Gly Ser Lys
            20

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1211

(xi) SEQUENCE DESCRIPTION: SEQ ID NO:4:

Glu Pro Leu Arg Thr Ser Val Asp Lys Pro Gly Ser Lys Lys Thr Gln
1               5                  10                  15

Gly Glu Lys Phe
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1212

(xi) SEQUENCE DESCRIPTION: SEQ ID NO:5:

Asp Lys Pro Gly Ser Lys Lys Thr Gln Gly Glu Lys Phe Phe Leu Ile
1               5                  10                  15

His Ser Ala Asp
            20

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: single
        (D) TOPOLOGY: linear
```

```
        (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1215

(xi) SEQUENCE DESCRIPTION: SEQ ID NO:6:

Leu Tyr Asn Glu Gln Phe Ala Val Gln Gly Leu Leu Arg Tyr His Thr
1               5                  10                  15

Tyr Ala Arg Phe
            20

(2) INFORMATION FOR SEQ ID NO:7:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1216

(xi) SEQUENCE DESCRIPTION: SEQ ID NO:7:

His Thr Tyr Ala Arg Phe Gly Ile Glu Ile Gln Val Gln Ile Asn Pro
1               5                  10                  15

Thr Pro Phe Gln
            20

(2) INFORMATION FOR SEQ ID NO:8:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1217

(xi) SEQUENCE DESCRIPTION: SEQ ID NO:8:

Ile Asn Pro Thr Pro Phe Gln Gln Gly Gly Leu Ile Cys Ala Met Val
1               5                  10                  15
```

```
Pro Gly Asp Gln
            20

(2) INFORMATION FOR SEQ ID NO:9:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1222

(xi) SEQUENCE DESCRIPTION: SEQ ID NO:9:

His Phe Lys Asp Pro Gln Tyr Pro Val Trp Glu Leu Thr Ile Arg Val
1               5                  10                  15

Trp Ser Glu Leu
            20

(2) INFORMATION FOR SEQ ID NO:10:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1224

(xi) SEQUENCE DESCRIPTION: SEQ ID NO:10:

Asn Ile Gly Thr Gly Thr Ser Ala Tyr Thr Ser Leu Asn Val Leu Ala
1               5                  10                  15

Arg Phe Thr Asp
            20

(2) INFORMATION FOR SEQ ID NO:11:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal
```

```
        (ix) FEATURE:
              (A) NAME/KEY: Peptide
              (B) LOCATION: 1..20
              (D) OTHER INFORMATION: /label= YK-1235

(xi) SEQUENCE DESCRIPTION: SEQ ID NO:11:

Ser Asp Pro Ser Gln Gly Gly Gly Ile Lys Ile Thr His Phe Thr Thr
1               5                   10                  15

Trp Thr Ser Ile
            20

(2) INFORMATION FOR SEQ ID NO:12:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
              (A) NAME/KEY: Peptide
              (B) LOCATION: 1..20
              (D) OTHER INFORMATION: /label= YK-1236

(xi) SEQUENCE DESCRIPTION: SEQ ID NO:12:

Gly Gly Ile Lys Ile Thr His Phe Thr Thr Trp Thr Ser Ile Pro Thr
1               5                   10                  15

Leu Ala Ala Gln
            20

(2) INFORMATION FOR SEQ ID NO:13:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
              (A) NAME/KEY: Peptide
              (B) LOCATION: 1..20
              (D) OTHER INFORMATION: /label= YK-1241

(xi) SEQUENCE DESCRIPTION: SEQ ID NO:13:

Gln Phe Pro Phe Asn Ala Ser Asp Ser Val Gly Gln Gln Ile Lys Val
1               5                   10                  15

Ile Pro Val Asp
            20

(2) INFORMATION FOR SEQ ID NO:14:

(i) SEQUENCE CHARACTERISTICS:
              (A) LENGTH: 20 amino acids
```

```
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1242

(xi) SEQUENCE DESCRIPTION: SEQ ID NO:14:

Phe Asn Ala Ser Asp Ser Val Gly Gln Gln Ile Lys Val Ile Pro Val
1               5                  10                  15

Asp Pro Tyr Phe
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1243

(xi) SEQUENCE DESCRIPTION: SEQ ID NO:15:

Ser Asp Ser Val Gly Gln Gln Ile Lys Val Ile Pro Val Asp Pro Tyr
1               5                  10                  15

Phe Phe Gln Met
            20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1244

(xi) SEQUENCE DESCRIPTION: SEQ ID NO:16:
```

```
Ile Lys Val Ile Pro Val Asp Pro Tyr Phe Phe Gln Met Thr Asn Thr
1               5                   10                  15

Asn Pro Asp Gln
            20
```

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1247

(xi) SEQUENCE DESCRIPTION: SEQ ID NO:17:

```
Lys Cys Ile Thr Ala Leu Ala Ser Ile Cys Gln Met Phe Cys Phe Trp
1               5                   10                  15

Arg Gly Asp Leu
            20
```

(2) INFORMATION FOR SEQ ID NO:18:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1248

(xi) SEQUENCE DESCRIPTION: SEQ ID NO:18:

```
Phe Trp Arg Gly Asp Leu Val Phe Asp Phe Gln Val Phe Pro Thr Lys
1               5                   10                  15

Tyr His Ser Gly
            20
```

(2) INFORMATION FOR SEQ ID NO:19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1249

(xi) SEQUENCE DESCRIPTION: SEQ ID NO:19:

Phe Asp Phe Gln Val Phe Pro Thr Lys Tyr His Ser Gly Arg Leu Leu
1               5                  10                  15

Phe Cys Phe Val
            20

(2) INFORMATION FOR SEQ ID NO:20:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1250

(xi) SEQUENCE DESCRIPTION: SEQ ID NO:20:

Phe Pro Thr Lys Tyr His Ser Gly Arg Leu Leu Phe Cys Phe Val Pro
1               5                  10                  15

Gly Asn Glu Leu
            20

(2) INFORMATION FOR SEQ ID NO:21:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1252

(xi) SEQUENCE DESCRIPTION: SEQ ID NO:21:

Gly Ile Thr Leu Lys Gln Ala Thr Thr Ala Pro Cys Ala Val Met Asp
1               5                  10                  15

Ile Thr Gly Val
            20

(2) INFORMATION FOR SEQ ID NO:22:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1261

(xi) SEQUENCE DESCRIPTION: SEQ ID NO:22:

Val Ala Ser His Val Arg Val Asn Val Tyr Leu Ser Ala Ile Asn Leu
1               5                   10                  15

Glu Cys Phe Ala
            20

(2) INFORMATION FOR SEQ ID NO:23:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1265

(xi) SEQUENCE DESCRIPTION: SEQ ID NO:23:

Thr Thr Val Ser Thr Glu Gln Asn Val Pro Asp Pro Gln Val Gly Ile
1               5                   10                  15

Thr Thr Met Lys
            20

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1266

(xi) SEQUENCE DESCRIPTION: SEQ ID NO:24:

Gln Asn Val Pro Asp Pro Gln Val Gly Ile Thr Thr Met Lys Asp Leu
1               5                  10                  15

Lys Gly Lys Ala
            20

(2) INFORMATION FOR SEQ ID NO:25:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
          (A) NAME/KEY: Peptide
          (B) LOCATION: 1..20
          (D) OTHER INFORMATION: /label= YK-1268

(xi) SEQUENCE DESCRIPTION: SEQ ID NO:25:

Asn Arg Gly Lys Met Asp Val Ser Gly Val Gln Ala Pro Val Gly Ala
1               5                  10                  15

Ile Thr Thr Ile
            20

(2) INFORMATION FOR SEQ ID NO:26:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
          (A) NAME/KEY: Peptide
          (B) LOCATION: 1..20
          (D) OTHER INFORMATION: /label= YK-1271

(xi) SEQUENCE DESCRIPTION: SEQ ID NO:26:

Ile Thr Thr Ile Glu Asp Pro Val Leu Ala Lys Lys Val Pro Glu Thr
1               5                  10                  15

Phe Pro Glu Leu
            20

(2) INFORMATION FOR SEQ ID NO:27:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide

```
        (iii) HYPOTHETICAL: NO (iv) ANTI-SENSE: NO (v) FRAGMENT TYPE: internal (ix) FEATURE:
              (A) NAME/KEY: Peptide
              (B) LOCATION: 1..20
              (D) OTHER INFORMATION: /label= YK-1272

(xi) SEQUENCE DESCRIPTION: SEQ ID NO:27:

Glu Asp Pro Val Leu Ala Lys Lys Val Pro Glu Thr Phe Pro Glu Leu
1               5                   10                  15

Lys Pro Gly Glu
            20

(2) INFORMATION FOR SEQ ID NO:28:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
              (A) NAME/KEY: Peptide
              (B) LOCATION: 1..20
              (D) OTHER INFORMATION: /label= YK-1273

(xi) SEQUENCE DESCRIPTION: SEQ ID NO:28:

Ala Lys Lys Val Pro Glu Thr Phe Pro Glu Leu Lys Pro Gly Glu Ser
1               5                   10                  15

Arg His Thr Ser
            20

(2) INFORMATION FOR SEQ ID NO:29:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
              (A) NAME/KEY: Peptide
              (B) LOCATION: 1..20
              (D) OTHER INFORMATION: /label= YK-1274

(xi) SEQUENCE DESCRIPTION: SEQ ID NO:29:

Phe Pro Glu Leu Lys Pro Gly Glu Ser Arg His Thr Ser Asp His Met
1               5                   10                  15

Ser Ile Tyr Lys
            20
```

(2) INFORMATION FOR SEQ ID NO:30:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1276

(xi) SEQUENCE DESCRIPTION: SEQ ID NO:30:

Asp His Met Ser Ile Tyr Lys Phe Met Gly Arg Ser His Phe Leu Cys
1               5                  10                  15

Thr Phe Thr Phe
            20

(2) INFORMATION FOR SEQ ID NO:31:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1279

(xi) SEQUENCE DESCRIPTION: SEQ ID NO:31:

His Phe Leu Cys Thr Phe Thr Phe Asn Ser Asn Asn Lys Glu Tyr Thr
1               5                  10                  15

Phe Pro Ile Thr
            20

(2) INFORMATION FOR SEQ ID NO:32:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:

(A) NAME/KEY: Peptide
            (B) LOCATION: 1..20
            (D) OTHER INFORMATION: /label= YK-1290

(xi) SEQUENCE DESCRIPTION: SEQ ID NO:32:

Thr Pro Val Gly Leu Ala Val Asp Thr Pro Trp Val Glu Lys Glu Ser
1               5                   10                  15

Ala Leu Ser Ile
            20

(2) INFORMATION FOR SEQ ID NO:33:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1307

(xi) SEQUENCE DESCRIPTION: SEQ ID NO:33:

Leu Ser Phe Ser Cys Tyr Leu Ser Val Thr Glu Gln Ser Glu Phe Tyr
1               5                   10                  15

Phe Pro Arg Ala
            20

(2) INFORMATION FOR SEQ ID NO:34:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1308

(xi) SEQUENCE DESCRIPTION: SEQ ID NO:34:

Ser Val Thr Glu Gln Ser Glu Phe Tyr Phe Pro Arg Ala Pro Leu Asn
1               5                   10                  15

Ser Asn Ala Met
            20

(2) INFORMATION FOR SEQ ID NO:35:

(i) SEQUENCE CHARACTERISTICS:
        (A) LENGTH: 20 amino acids
        (B) TYPE: amino acid
        (C) STRANDEDNESS: single

```
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1310

(xi) SEQUENCE DESCRIPTION: SEQ ID NO:35:

Pro Leu Asn Ser Asn Ala Met Leu Ser Thr Glu Ser Met Met Ser Arg
1               5                   10                  15

Ile Ala Ala Gly
            20

(2) INFORMATION FOR SEQ ID NO:36:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1312

(xi) SEQUENCE DESCRIPTION: SEQ ID NO:36:

Met Ser Arg Ile Ala Ala Gly Asp Leu Glu Ser Ser Val Asp Pro
1               5                   10                  15

Arg Ser Glu Glu
            20

(2) INFORMATION FOR SEQ ID NO:37:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1313

(xi) SEQUENCE DESCRIPTION: SEQ ID NO:37:

Ala Gly Asp Leu Glu Ser Ser Val Asp Pro Arg Ser Glu Glu Asp
1               5                   10                  15
```

```
Lys Arg Phe Glu
        20

(2) INFORMATION FOR SEQ ID NO:38:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1314

(xi) SEQUENCE DESCRIPTION: SEQ ID NO:38:

Val Asp Asp Pro Arg Ser Glu Glu Asp Lys Arg Phe Glu Ser His Ile
1               5                   10                  15

Glu Cys Arg Lys
        20

(2) INFORMATION FOR SEQ ID NO:39:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1315

(xi) SEQUENCE DESCRIPTION: SEQ ID NO:39:

Ser His Ile Glu Cys Arg Lys Pro Tyr Lys Glu Leu Arg Leu Glu Val
1               5                   10                  15

Gly Lys Gln Arg
        20

(2) INFORMATION FOR SEQ ID NO:40:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO
```

```
        (v) FRAGMENT TYPE: internal (ix) FEATURE:
             (A) NAME/KEY: Peptide
             (B) LOCATION: 1..20
             (D) OTHER INFORMATION: /label= YK-1316

(xi) SEQUENCE DESCRIPTION: SEQ ID NO:40:

Pro Tyr Lys Glu Leu Arg Leu Glu Val Gly Lys Gln Arg Leu Lys Tyr
1               5                   10                  15

Ala Gln Glu Glu
            20

(2) INFORMATION FOR SEQ ID NO:41:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1317

(xi) SEQUENCE DESCRIPTION: SEQ ID NO:41:

Gln Arg Leu Lys Tyr Ala Gln Glu Glu Leu Ser Asn Glu Val Leu Pro
1               5                   10                  15

Pro Pro Arg Lys
            20

(2) INFORMATION FOR SEQ ID NO:42:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1318

(xi) SEQUENCE DESCRIPTION: SEQ ID NO:42:

Val Leu Pro Pro Pro Arg Lys Met Lys Gly Leu Phe Ser Gln Ala Lys
1               5                   10                  15

Ile Ser Leu Phe
            20

(2) INFORMATION FOR SEQ ID NO:43:

(i) SEQUENCE CHARACTERISTICS:
```

(A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Peptide
            (B) LOCATION: 1..20
            (D) OTHER INFORMATION: /label= YK-1319

(xi) SEQUENCE DESCRIPTION: SEQ ID NO:43:

Phe Ser Gln Ala Lys Ile Ser Leu Phe Tyr Thr Glu Glu His Glu Ile
1               5                  10                  15

Met Lys Phe Ser
            20

(2) INFORMATION FOR SEQ ID NO:44:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Peptide
            (B) LOCATION: 1..20
            (D) OTHER INFORMATION: /label= YK-1327

(xi) SEQUENCE DESCRIPTION: SEQ ID NO:44:

Lys Val Asn Phe Pro His Gly Met Leu Asp Leu Glu Glu Ile Ala Ala
1               5                  10                  15

Asn Ser Lys Asp
            20

(2) INFORMATION FOR SEQ ID NO:45:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Peptide
            (B) LOCATION: 1..20
            (D) OTHER INFORMATION: /label= YK-1328

(xi) SEQUENCE DESCRIPTION: SEQ ID NO:45:

```
Asp Leu Glu Glu Ile Ala Ala Asn Ser Lys Asp Phe Pro Asn Met Ser
1               5                   10                  15

Glu Thr Asp Leu
            20

(2) INFORMATION FOR SEQ ID NO:46:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1331

(xi) SEQUENCE DESCRIPTION: SEQ ID NO:46:

Lys Ile Asn Leu Ala Asp Arg Met Leu Gly Leu Ser Gly Val Gln Glu
1               5                   10                  15

Ile Lys Glu Gln
            20

(2) INFORMATION FOR SEQ ID NO:47:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..25
        (D) OTHER INFORMATION: /label= YK-1665

(xi) SEQUENCE DESCRIPTION: SEQ ID NO:47:

Gln Arg Leu Lys Tyr Ala Gln Glu Glu Leu Ser Asn Glu Val Leu Pro
1               5                   10                  15

Pro Pro Arg Lys Met Lys Gly Leu Phe
            20                  25

(2) INFORMATION FOR SEQ ID NO:48:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO
```

```
        (iv) ANTI-SENSE: NO (v) FRAGMENT TYPE: internal (ix) FEATURE:
             (A) NAME/KEY: Peptide
             (B) LOCATION: 1..25
             (D) OTHER INFORMATION: /label= YK-1757

(xi) SEQUENCE DESCRIPTION: SEQ ID NO:48:

Trp Leu Asn Pro Lys Lys Ile Asn Leu Ala Asp Arg Met Leu Gly Leu
1               5                  10                  15

Ser Gly Val Gln Glu Ile Lys Glu Gln
            20                  25

(2) INFORMATION FOR SEQ ID NO:49:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1334

(xi) SEQUENCE DESCRIPTION: SEQ ID NO:49:

Val Ile Gln Gln Leu Asn Gln Asp Glu His Ser His Ile Ile Gly Leu
1               5                  10                  15

Leu Arg Val Met
            20

(2) INFORMATION FOR SEQ ID NO:50:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1341

(xi) SEQUENCE DESCRIPTION: SEQ ID NO:50:

Asn Ile Leu Lys Asp Asn Gln Gln Lys Ile Glu Lys Ala Ile Glu Glu
1               5                  10                  15

Ala Asp Glu Phe
            20
```

(2) INFORMATION FOR SEQ ID NO:51:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1347

(xi) SEQUENCE DESCRIPTION: SEQ ID NO:51:

```
Leu Gly Ser Ile Asn Gln Ala Met Val Thr Arg Cys Glu Pro Val Val
  1               5                  10                  15
Cys Tyr Leu Tyr
            20
```

(2) INFORMATION FOR SEQ ID NO:52:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1348

(xi) SEQUENCE DESCRIPTION: SEQ ID NO:52:

```
Arg Cys Glu Pro Val Val Cys Tyr Leu Tyr Gly Lys Arg Gly Gly Gly
  1               5                  10                  15
Lys Ser Leu Thr
            20
```

(2) INFORMATION FOR SEQ ID NO:53:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20

(D) OTHER INFORMATION: /label= YK-1352

(xi) SEQUENCE DESCRIPTION: SEQ ID NO:53:

Thr Lys Pro Val Ala Ser Asp Tyr Trp Asp Gly Tyr Ser Gly Gln Leu
1               5                   10                  15

Val Cys Ile Ile
            20

(2) INFORMATION FOR SEQ ID NO:54:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1356

(xi) SEQUENCE DESCRIPTION: SEQ ID NO:54:

Val Ser Gly Cys Pro Met Arg Leu Asn Met Ala Ser Leu Glu Glu Lys
1               5                   10                  15

Gly Arg His Phe
            20

(2) INFORMATION FOR SEQ ID NO:55:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1357

(xi) SEQUENCE DESCRIPTION: SEQ ID NO:55:

Leu Asn Met Ala Ser Leu Glu Glu Lys Gly Arg His Phe Ser Ser Pro
1               5                   10                  15

Phe Ile Ile Ala
            20

(2) INFORMATION FOR SEQ ID NO:56:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1360

(xi) SEQUENCE DESCRIPTION: SEQ ID NO:56:

Asn Pro Ser Pro Lys Thr Val Tyr Val Lys Glu Ala Ile Asp Arg Arg
  1               5                  10                  15

Leu His Phe Lys
             20

(2) INFORMATION FOR SEQ ID NO:57:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1361

(xi) SEQUENCE DESCRIPTION: SEQ ID NO:57:

Val Lys Glu Ala Ile Asp Arg Arg Leu His Phe Lys Val Glu Val Lys
  1               5                  10                  15

Pro Ala Ser Phe
             20

(2) INFORMATION FOR SEQ ID NO:58:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1..20
             (D) OTHER INFORMATION: /label= YK-1362

(xi) SEQUENCE DESCRIPTION: SEQ ID NO:58:

Val Lys Pro Ala Ser Phe Phe Lys Asn Pro His Asn Asp Met Leu Asn
  1               5                  10                  15

Val Asn Leu Ala

20

(2) INFORMATION FOR SEQ ID NO:59:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1363

(xi) SEQUENCE DESCRIPTION: SEQ ID NO:59:

Lys Asn Pro His Asn Asp Met Leu Asn Val Asn Leu Ala Lys Thr Asn
1               5                  10                  15

Asp Ala Ile Lys
            20

(2) INFORMATION FOR SEQ ID NO:60:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1364

(xi) SEQUENCE DESCRIPTION: SEQ ID NO:60:

Leu Ala Lys Thr Asn Asp Ala Ile Lys Asp Met Ser Cys Val Asp Leu
1               5                  10                  15

Ile Met Asp Gly
            20

(2) INFORMATION FOR SEQ ID NO:61:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal

```
    (ix) FEATURE:
         (A) NAME/KEY: Peptide
         (B) LOCATION: 1..20
         (D) OTHER INFORMATION: /label= YK-1367

(xi) SEQUENCE DESCRIPTION: SEQ ID NO:61:

Val Met Thr Val Glu Ile Arg Lys Gln Asn Met Thr Glu Phe Met Glu
1               5                   10                  15

Leu Trp Ser Gln
            20

(2) INFORMATION FOR SEQ ID NO:62:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1368

(xi) SEQUENCE DESCRIPTION: SEQ ID NO:62:

Ser Gln Gly Ile Ser Asp Asp Asp Asn Asp Ser Ala Val Ala Glu Phe
1               5                   10                  15

Phe Gln Ser Phe
            20

(2) INFORMATION FOR SEQ ID NO:63:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1369

(xi) SEQUENCE DESCRIPTION: SEQ ID NO:63:

Asp Ser Ala Val Ala Glu Phe Phe Gln Ser Phe Pro Ser Gly Glu Pro
1               5                   10                  15

Ser Asn Ser Lys
            20

(2) INFORMATION FOR SEQ ID NO:64:

(i) SEQUENCE CHARACTERISTICS:
         (A) LENGTH: 20 amino acids
         (B) TYPE: amino acid
```

-continued

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Peptide
            (B) LOCATION: 1..20
            (D) OTHER INFORMATION: /label= YK-1370

(xi) SEQUENCE DESCRIPTION: SEQ ID NO:64:

Phe Gln Ser Phe Pro Ser Gly Glu Pro Ser Asn Ser Lys Leu Ser Gly
1               5                  10                  15

Phe Phe Gln Ser
            20

(2) INFORMATION FOR SEQ ID NO:65:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Peptide
            (B) LOCATION: 1..25
            (D) OTHER INFORMATION: /label= YK-1832

(xi) SEQUENCE DESCRIPTION: SEQ ID NO:65:

Ser Ala Val Ala Glu Phe Phe Gln Ser Phe Pro Ser Gly Glu Pro Ser
1               5                  10                  15

Asn Ser Lys Leu Ser Gly Phe Phe Gln
            20                  25

(2) INFORMATION FOR SEQ ID NO:66:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Peptide
            (B) LOCATION: 1..20
            (D) OTHER INFORMATION: /label= YK-1374

(xi) SEQUENCE DESCRIPTION: SEQ ID NO:66:

His Gly Val Thr Lys Pro Lys Gln Val Ile Lys Leu Asp Ala Asp Pro
```

```
                1               5                  10                 15
Val Glu Ser Gln
            20

(2) INFORMATION FOR SEQ ID NO:67:

(i) SEQUENCE CHARACTERISTICS:
           (A) LENGTH: 20 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
           (A) NAME/KEY: Peptide
           (B) LOCATION: 1..20
           (D) OTHER INFORMATION: /label= YK-1376

(xi) SEQUENCE DESCRIPTION: SEQ ID NO:67:

Gly Leu Val Arg Lys Asn Leu Val Gln Phe Gly Val Gly Glu Lys Asn
1               5                  10                 15
Gly Cys Val Arg
            20

(2) INFORMATION FOR SEQ ID NO:68:

(i) SEQUENCE CHARACTERISTICS:
           (A) LENGTH: 20 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
           (A) NAME/KEY: Peptide
           (B) LOCATION: 1..20
           (D) OTHER INFORMATION: /label= YK-1382

(xi) SEQUENCE DESCRIPTION: SEQ ID NO:68:

Asp Val Val Leu Met Lys Val Pro Thr Ile Pro Lys Phe Arg Asp Ile
1               5                  10                 15
Thr Gln His Phe
            20

(2) INFORMATION FOR SEQ ID NO:69:

(i) SEQUENCE CHARACTERISTICS:
           (A) LENGTH: 20 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO
```

(v) FRAGMENT TYPE: internal (ix) FEATURE:
           (A) NAME/KEY: Peptide
           (B) LOCATION: 1..20
           (D) OTHER INFORMATION: /label= YK-1388

(xi) SEQUENCE DESCRIPTION: SEQ ID NO:69:

Met Glu Glu Lys Ala Thr Tyr Val His Lys Lys Asn Asp Gly Thr Thr
1               5                   10                  15

Val Asp Leu Thr
            20

(2) INFORMATION FOR SEQ ID NO:70:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
           (A) NAME/KEY: Peptide
           (B) LOCATION: 1..20
           (D) OTHER INFORMATION: /label= YK-1389

(xi) SEQUENCE DESCRIPTION: SEQ ID NO:70:

Lys Asn Asp Gly Thr Thr Val Asp Leu Thr Val Asp Gln Ala Trp Arg
1               5                   10                  15

Gly Lys Gly Glu
            20

(2) INFORMATION FOR SEQ ID NO:71:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
           (A) NAME/KEY: Peptide
           (B) LOCATION: 1..20
           (D) OTHER INFORMATION: /label= YK-1390

(xi) SEQUENCE DESCRIPTION: SEQ ID NO:71:

Arg Gly Lys Gly Glu Gly Leu Pro Gly Met Cys Gly Gly Ala Leu Val
1               5                   10                  15

Ser Ser Asn Gln
            20

(2) INFORMATION FOR SEQ ID NO:72:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1393

(xi) SEQUENCE DESCRIPTION: SEQ ID NO:72:

Val Ala Lys Leu Val Thr Gln Glu Met Phe Gln Asn Ile Asp Lys Lys
1               5                  10                  15

Ile Glu Ser Gln
          20

(2) INFORMATION FOR SEQ ID NO:73:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1394

(xi) SEQUENCE DESCRIPTION: SEQ ID NO:73:

Arg Ile Met Lys Val Glu Phe Thr Gln Cys Ser Met Asn Val Val Ser
1               5                  10                  15

Lys Thr Leu Phe
          20

(2) INFORMATION FOR SEQ ID NO:74:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1395

(xi) SEQUENCE DESCRIPTION: SEQ ID NO:74:

Phe Thr Gln Cys Ser Met Asn Val Val Ser Lys Thr Leu Phe Arg Lys
1               5                   10                  15

Ser Pro Ile Tyr
            20

(2) INFORMATION FOR SEQ ID NO:75:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1399

(xi) SEQUENCE DESCRIPTION: SEQ ID NO:75:

Met Leu Ser Lys Tyr Ser Leu Pro Ile Val Glu Glu Pro Glu Asp Tyr
1               5                   10                  15

Lys Glu Ala Ser
            20

(2) INFORMATION FOR SEQ ID NO:76:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1407

(xi) SEQUENCE DESCRIPTION: SEQ ID NO:76:

Leu Asp Glu Asn Gly Leu Leu Leu Gly Val His Pro Arg Leu Ala Gln
1               5                   10                  15

Arg Ile Leu Phe
            20

(2) INFORMATION FOR SEQ ID NO:77:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide

```
    (iii) HYPOTHETICAL: NO (iv) ANTI-SENSE: NO (v) FRAGMENT TYPE: internal (ix) FEATURE:
          (A) NAME/KEY: Peptide
          (B) LOCATION: 1..20
          (D) OTHER INFORMATION: /label= YK-1411

(xi) SEQUENCE DESCRIPTION: SEQ ID NO:77:

Cys Pro Lys Asp Glu Leu Arg Pro Leu Glu Lys Val Leu Glu Ser Lys
1               5                  10                  15

Thr Arg Ala Ile
            20

(2) INFORMATION FOR SEQ ID NO:78:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
          (A) NAME/KEY: Peptide
          (B) LOCATION: 1..20
          (D) OTHER INFORMATION: /label= YK-1412

(xi) SEQUENCE DESCRIPTION: SEQ ID NO:78:

Ser Lys Thr Arg Ala Ile Asp Ala Cys Pro Leu Asp Tyr Ser Ile Leu
1               5                  10                  15

Cys Arg Met Tyr
            20

(2) INFORMATION FOR SEQ ID NO:79:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
          (A) NAME/KEY: Peptide
          (B) LOCATION: 1..20
          (D) OTHER INFORMATION: /label= YK-1414

(xi) SEQUENCE DESCRIPTION: SEQ ID NO:79:

Arg Met Tyr Trp Gly Pro Ala Ile Ser Tyr Phe His Leu Asn Pro Gly
1               5                  10                  15

Phe His Thr Gly
            20
```

(2) INFORMATION FOR SEQ ID NO:80:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1418

(xi) SEQUENCE DESCRIPTION: SEQ ID NO:80:

Lys Thr Met Ile Arg Phe Gly Asp Val Gly Leu Asp Leu Asp Phe Ser
1               5                   10                  15

Ala Phe Asp Ala
        20

(2) INFORMATION FOR SEQ ID NO:81:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1419

(xi) SEQUENCE DESCRIPTION: SEQ ID NO:81:

Asp Leu Asp Phe Ser Ala Phe Asp Ala Ser Leu Ser Pro Phe Met Ile
1               5                   10                  15

Arg Glu Ala Gly
        20

(2) INFORMATION FOR SEQ ID NO:82:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide (B) LOCATION: 1..20
        (D) OTHER INFORMATION: /label= YK-1424

(xi) SEQUENCE DESCRIPTION: SEQ ID NO:82:

Ile Asn Asn Val Asn Leu Tyr Tyr Val Phe Ser Lys Ile Phe Gly Lys
1               5                   10                  15

Ser Pro Val Phe
            20

(2) INFORMATION FOR SEQ ID NO:83:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1428

(xi) SEQUENCE DESCRIPTION: SEQ ID NO:83:

Gly Gln Lys Ile Val Asp Glu Phe Lys Lys Leu Gly Met Thr Ala Thr
1               5                   10                  15

Ser Ala Asp Lys
            20

(2) INFORMATION FOR SEQ ID NO:84:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..20
        (D) OTHER INFORMATION: /label= YK-1429

(xi) SEQUENCE DESCRIPTION: SEQ ID NO:84:

Leu Gly Met Thr Ala Thr Ser Ala Asp Lys Asn Val Pro Gln Leu Lys
1               5                   10                  15

Pro Val Ser Glu
            20

(2) INFORMATION FOR SEQ ID NO:85:

(i) SEQUENCE CHARACTERISTICS:
        (A) LENGTH: 20 amino acids
        (B) TYPE: amino acid
        (C) STRANDEDNESS: single
        (D) TOPOLOGY: linear

```
    (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1431

(xi) SEQUENCE DESCRIPTION: SEQ ID NO:85:

Pro Gln Leu Lys Pro Val Ser Glu Leu Thr Phe Leu Lys Arg Ser Phe
1               5                  10                  15

Asn Leu Val Glu
            20

(2) INFORMATION FOR SEQ ID NO:86:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1434

(xi) SEQUENCE DESCRIPTION: SEQ ID NO:86:

Ser Glu Lys Thr Ile Trp Ser Leu Ile Ala Trp Gln Arg Ser Asn Ala
1               5                  10                  15

Glu Phe Glu Gln
            20

(2) INFORMATION FOR SEQ ID NO:87:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 1..20
         (D) OTHER INFORMATION: /label= YK-1435

(xi) SEQUENCE DESCRIPTION: SEQ ID NO:87:

Ser Leu Ile Ala Trp Gln Arg Ser Asn Ala Glu Phe Glu Gln Asn Leu
1               5                  10                  15
```

-continued

```
Glu Asn Ala Gln
            20

(2) INFORMATION FOR SEQ ID NO:88:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
          (A) NAME/KEY: Peptide
          (B) LOCATION: 1..20
          (D) OTHER INFORMATION: /label= YK-1436

(xi) SEQUENCE DESCRIPTION: SEQ ID NO:88:

Trp Gln Arg Ser Asn Ala Glu Phe Glu Gln Asn Leu Glu Asn Ala Gln
1               5                   10                  15

Trp Phe Ala Phe
            20
```